(12) United States Patent
Denison et al.

(10) Patent No.: US 8,371,315 B2
(45) Date of Patent: Feb. 12, 2013

(54) WASHING SYSTEMS INCORPORATING CHARGED ACTIVATED LIQUIDS

(75) Inventors: Thomas R. Denison, Newport Coast, CA (US); Bruce F. Field, Golden Valley, MN (US); Jonathan A. Zimmerman, London (GB)

(73) Assignee: Tennant Company, Minneapolis, MN (US)

( * ) Notice: Subject to any disclaimer, the term of this patent is extended or adjusted under 35 U.S.C. 154(b) by 372 days.

(21) Appl. No.: 12/693,114

(22) Filed: Jan. 25, 2010

(65) Prior Publication Data

US 2010/0181208 A1 Jul. 22, 2010

Related U.S. Application Data

(63) Continuation-in-part of application No. 12/639,622, filed on Dec. 16, 2009, and a continuation-in-part of application No. 12/639,628, filed on Dec. 16, 2009.

(60) Provisional application No. 61/146,903, filed on Jan. 23, 2009, provisional application No. 61/138,465, filed on Dec. 17, 2008, provisional application No. 61/248,557, filed on Oct. 5, 2009, provisional application No. 61/138,465, filed on Dec. 17, 2008, provisional application No. 61/248,557, filed on Oct. 5, 2009.

(51) Int. Cl.
*B08B 3/00* (2006.01)

(52) U.S. Cl. ............... 134/60; 134/58 R; 134/58 D; 15/3

(58) Field of Classification Search .................. None
See application file for complete search history.

(56) References Cited

U.S. PATENT DOCUMENTS

| | | | |
|---|---|---|---|
| 3,859,195 A | 1/1975 | Williams | 204/272 |
| 3,933,614 A | 1/1976 | Bunn, Jr. | 204/266 |
| 4,099,489 A | 7/1978 | Bradley | 123/3 |
| 4,108,052 A | 8/1978 | Cunningham | 99/275 |
| 4,121,543 A | 10/1978 | Hicks, Jr. et al. | 123/3 |
| 4,154,578 A | 5/1979 | Bane | 8/137 |
| 4,244,079 A | 1/1981 | Bane | 15/321 |
| 4,502,929 A | 3/1985 | Stewart et al. | 204/147 |
| 4,630,167 A | 12/1986 | Huggins | 361/213 |
| 4,663,091 A | 5/1987 | Seo | 261/72.1 |
| 4,670,113 A | 6/1987 | Lewis | 204/80 |
| 4,676,882 A | 6/1987 | Okazaki | 204/260 |
| 4,687,558 A | 8/1987 | Justice et al. | 204/59 |
| 4,705,191 A | 11/1987 | Itzel et al. | 222/80 |
| 4,810,344 A | 3/1989 | Okazaki | 204/228 |
| 4,832,230 A | 5/1989 | Janowitz | 222/80 |
| 4,875,988 A | 10/1989 | Aragon | 204/265 |
| 5,186,860 A | 2/1993 | Joyce, Jr. et al. | 252/500 |
| 5,316,646 A | 5/1994 | Arai | 204/306 |

(Continued)

FOREIGN PATENT DOCUMENTS

| | | |
|---|---|---|
| AU | 732602 | 4/2001 |
| CN | 200977495 | 11/2007 |

(Continued)

OTHER PUBLICATIONS

Final Office Action from the United States Patent and Trademark Office for U.S. Appl. No. 11/655,378, dated Jul. 2, 2010.

(Continued)

*Primary Examiner* — Eric Golightly

(74) *Attorney, Agent, or Firm* — David D. Brush; Westman, Champlin & Kelly, P.A.

(57) ABSTRACT

A washing system comprising a washing machine vessel, a fluid-treatment component for activating a liquid, a dispenser for dispensing the activated liquid to the washing machine vessel, an electrode in electrical contact with the activated liquid, and at least one control circuit configured to generate an alternating electrical field through the dispensed activated liquid between the electrode and the washing machine vessel.

19 Claims, 14 Drawing Sheets

U.S. PATENT DOCUMENTS

| | | | |
|---|---|---|---|
| 5,320,718 A | 6/1994 | Molter et al. | 204/101 |
| 5,378,339 A | 1/1995 | Aoki et al. | 204/260 |
| 5,536,389 A | 7/1996 | La Naour et al. | 205/688 |
| 5,590,439 A | 1/1997 | Alazet | 15/320 |
| 5,632,870 A | 5/1997 | Kucherov | 204/241 |
| 5,665,212 A | 9/1997 | Zhong et al. | 304/297 |
| 5,766,438 A | 6/1998 | Ishibashi et al. | 204/520 |
| 5,779,891 A | 7/1998 | Andelman | 210/198.2 |
| 5,815,869 A | 10/1998 | Hopkins | 8/158 |
| 5,858,202 A | 1/1999 | Nakamura | 205/746 |
| 5,928,505 A | 7/1999 | Inakagata et al. | 210/91 |
| 5,931,859 A | 8/1999 | Burke | 607/66 |
| 6,016,973 A | 1/2000 | Thompson et al. | 239/304 |
| 6,032,655 A | 3/2000 | Kavonius | 123/538 |
| 6,088,211 A | 7/2000 | Pitel | 361/212 |
| 6,101,671 A | 8/2000 | Wright et al. | 15/365 |
| 6,110,353 A | 8/2000 | Hough | 205/790 |
| 6,132,572 A | 10/2000 | Kim | 204/253 |
| 6,200,434 B1 | 3/2001 | Shinjo et al. | 204/230.2 |
| 6,231,747 B1 | 5/2001 | Fukuzuka et al. | 205/500 |
| 6,315,886 B1 | 11/2001 | Zappi et al. | 205/701 |
| 6,379,628 B2 | 4/2002 | de Jong et al. | 422/186.04 |
| 6,425,958 B1 | 7/2002 | Giddings et al. | 134/21 |
| 6,488,016 B2 | 12/2002 | Kavonius | 123/538 |
| 6,502,766 B1 | 1/2003 | Streutker et al. | 239/332 |
| 6,585,827 B2 | 7/2003 | Field et al. | 134/6 |
| 6,638,364 B2 | 10/2003 | Harkins et al. | 134/21 |
| 6,652,719 B1 | 11/2003 | Tseng | 204/257 |
| 6,689,262 B2 | 2/2004 | Senkiw | 204/278.5 |
| 6,703,785 B2 | 3/2004 | Aiki et al. | 315/111.81 |
| 6,719,891 B2 | 4/2004 | Ruhr et al. | 205/500 |
| 6,735,812 B2 | 5/2004 | Hekman et al. | 15/320 |
| 6,855,233 B2 | 2/2005 | Sawada | 204/263 |
| 6,878,287 B1 | 4/2005 | Marais | 210/748 |
| 6,921,743 B2 | 7/2005 | Scheper et al. | 510/220 |
| 6,926,819 B2 | 8/2005 | Nakamura et al. | 205/701 |
| 6,964,739 B2 | 11/2005 | Boyd et al. | 210/167 |
| 6,974,561 B1 | 12/2005 | Thomason | 422/186.29 |
| 7,011,739 B2 | 3/2006 | Harkins et al. | 205/701 |
| 7,059,013 B2 | 6/2006 | Wydra et al. | 15/345 |
| 7,156,962 B2 | 1/2007 | Koizumi et al. | 204/292 |
| 7,160,472 B2 | 1/2007 | Van Vliet et al. | 201/748 |
| 7,226,542 B2 | 6/2007 | Zemel et al. | 210/748 |
| 7,238,272 B2 | 7/2007 | Sano | 205/701 |
| 2001/0002500 A1 | 6/2001 | Kasen et al. | 15/320 |
| 2001/0034922 A1 | 11/2001 | Ko | 15/320 |
| 2002/0023847 A1 | 2/2002 | Natsume | 205/687 |
| 2002/0032141 A1 | 3/2002 | Harkins | 510/253 |
| 2002/0112314 A1 | 8/2002 | Harkins | 15/321 |
| 2002/0185423 A1 | 12/2002 | Boyd et al. | 210/167 |
| 2003/0001439 A1 | 1/2003 | Schur | 310/11 |
| 2003/0070919 A1 | 4/2003 | Gilmore | 204/275.1 |
| 2003/0102270 A1 | 6/2003 | Schoeberl | 210/748 |
| 2003/0159230 A1 | 8/2003 | Oh | 15/320 |
| 2003/0159231 A1 | 8/2003 | Oh | 15/320 |
| 2003/0159233 A1 | 8/2003 | Oh | 15/321 |
| 2003/0164306 A1 | 9/2003 | Senkiw | 205/633 |
| 2003/0213505 A1 | 11/2003 | Price et al. | 134/25.2 |
| 2004/0011665 A1 | 1/2004 | Koizumi et al. | 205/626 |
| 2004/0012913 A1 | 1/2004 | Andelman | 361/503 |
| 2004/0069611 A1 | 4/2004 | MacGregor | 204/157.15 |
| 2004/0112763 A1 | 6/2004 | Itoh et al. | 205/746 |
| 2004/0166019 A1 | 8/2004 | Schultheiss | 422/19 |
| 2004/0168933 A1 | 9/2004 | Inoue | 205/746 |
| 2004/0226123 A1 | 11/2004 | Policicchio et al. | 15/115 |
| 2004/0250323 A1 | 12/2004 | Arai et al. | D32/1 |
| 2004/0256247 A1 | 12/2004 | Carson et al. | 205/688 |
| 2005/0126928 A1 | 6/2005 | Hung et al. | 205/746 |
| 2005/0136520 A1 | 6/2005 | Kinley et al. | 435/155 |
| 2005/0139239 A1 | 6/2005 | Prae | 134/34 |
| 2005/0139808 A1 | 6/2005 | Alimi | 252/187.26 |
| 2005/0194261 A1 | 9/2005 | Hadia | 205/746 |
| 2005/0244556 A1 | 11/2005 | Karren | 426/335 |
| 2006/0037869 A1 | 2/2006 | Mitchke | 205/701 |
| 2006/0076248 A1 | 4/2006 | Kindred | 205/743 |
| 2006/0162735 A1 | 7/2006 | Thiebaut | 132/200 |
| 2006/0169575 A1 | 8/2006 | Sumita | 204/164 |
| 2006/0231503 A1 | 10/2006 | Flettner | 210/748 |
| 2006/0280664 A1 | 12/2006 | Huang et al. | 422/292 |
| 2007/0023273 A1 | 2/2007 | Kitaori et al. | 204/164 |
| 2007/0037267 A1 | 2/2007 | Lewis et al. | 435/161 |
| 2007/0141434 A1 | 6/2007 | Joshi et al. | 429/34 |
| 2007/0170072 A1 | 7/2007 | Shyu | 205/701 |
| 2007/0186367 A1 | 8/2007 | Field et al. | 15/320 |
| 2007/0186368 A1 | 8/2007 | Field et al. | 15/320 |
| 2007/0186957 A1 | 8/2007 | Field et al. | 134/18 |
| 2007/0186958 A1 | 8/2007 | Field et al. | 134/21 |
| 2007/0187263 A1 | 8/2007 | Field et al. | 205/742 |
| 2008/0264778 A1 | 10/2008 | Joshi et al. | 204/232 |
| 2009/0184186 A1 | 7/2009 | Suda et al. | 239/690 |

FOREIGN PATENT DOCUMENTS

| | | |
|---|---|---|
| DE | 2951993 | 7/1981 |
| DE | 8430251 | 6/1984 |
| DE | 4406320 | 8/1995 |
| DE | 19752174 | 7/1998 |
| DE | 202004010572 | 11/2004 |
| EP | 0041373 | 12/1981 |
| EP | 0104345 | 4/1984 |
| EP | 0199493 | 10/1986 |
| EP | 0438902 | 7/1991 |
| EP | 0636581 | 2/1995 |
| EP | 0663176 | 7/1995 |
| EP | 0672623 | 9/1995 |
| EP | 0761235 | 3/1997 |
| EP | 1000554 | 5/2000 |
| EP | 1008662 | 6/2000 |
| EP | 1188719 | 3/2002 |
| EP | 1293481 | 3/2003 |
| EP | 1308421 | 5/2003 |
| EP | 1065170 | 1/2004 |
| EP | 1386995 | 2/2004 |
| EP | 1309519 | 9/2004 |
| EP | 1533041 | 5/2005 |
| EP | 1671560 | 6/2006 |
| EP | 1741676 | 1/2007 |
| EP | 1754804 | 2/2007 |
| EP | 1903128 | 3/2008 |
| EP | 1932809 | 6/2008 |
| EP | 1941912 | 7/2008 |
| EP | 1978142 | 10/2008 |
| FR | 2381835 | 9/1978 |
| FR | 2909370 | 6/2008 |
| GB | 611819 | 11/1948 |
| GB | 2149423 | 11/1983 |
| GB | 2141738 | 1/1985 |
| GB | 2381187 | 4/2003 |
| GB | 2393737 | 4/2004 |
| JP | 1111483 | 4/1989 |
| JP | 07233493 | 9/1995 |
| JP | 1997-174054 | 7/1997 |
| JP | 11090442 | 9/1997 |
| JP | 11010159 | 1/1999 |
| JP | 2000-079393 | 3/2000 |
| JP | 2003-062573 | 3/2003 |
| JP | 2003-181338 | 7/2003 |
| JP | 2003-261190 | 9/2003 |
| JP | 2003-3266073 | 9/2003 |
| JP | 2003-334557 | 11/2003 |
| JP | 2004-129954 | 4/2004 |
| JP | 2004-148108 | 5/2004 |
| JP | 2004-148109 | 5/2004 |
| JP | 2006-036341 | 9/2006 |
| JP | 2007-000402 | 1/2007 |
| JP | 2007-239041 | 9/2007 |
| KR | 100599229 | 7/2006 |
| NL | 1012257 | 12/2000 |
| WO | 8606098 | 10/1986 |
| WO | 9640591 | 12/1995 |
| WO | 9818723 | 5/1998 |
| WO | 9846874 | 10/1998 |
| WO | 9908719 | 2/1999 |
| WO | 9963843 | 12/1999 |
| WO | 0214228 | 2/2002 |
| WO | 02066382 | 8/2002 |
| WO | 03009920 | 2/2003 |
| WO | 03022444 | 3/2003 |

| | | |
|---|---|---|
| WO | 03040038 | 5/2003 |
| WO | 2004079051 | 9/2004 |
| WO | 2004106242 | 12/2004 |
| WO | 2004108607 | 12/2004 |
| WO | 2005014058 | 2/2005 |
| WO | 2005097350 | 10/2005 |
| WO | 2005012186 | 2/2006 |
| WO | 2006124805 | 11/2006 |
| WO | 20070031779 | 3/2007 |
| WO | 2007095072 | 8/2007 |
| WO | 2007095074 | 8/2007 |
| WO | 2007138363 | 12/2007 |
| WO | 2007142693 | 12/2007 |
| WO | 2007145058 | 12/2007 |
| WO | 2007145385 | 12/2007 |
| WO | 2008032544 | 3/2008 |
| WO | 2008061546 | 5/2008 |
| WO | 2008131389 | 10/2008 |

OTHER PUBLICATIONS

Written Opinion dated May 20, 2010 from International Application No. PCT/US2010/021974, filed Jan. 25, 2010.

International Search Report dated May 20, 2010 from International Application No. PCT/US2010/021974, filed Jan. 25, 2010.

Bluhm, Hans J. et al., "Disruption and Destruction of Biological Cells Using Strong Pulsed Electric Fields" Nachrichten, Karlsruhe, DE, vol. 3, Jan. 1, 2005, pp. 105-110.

"Conductive Polymers: Evaluation if Industrial Applications" Synthetic Metals, 55-57 (1993) 3623-3631 S. Roth et al.

"ECO Smarte—The Best Multiple Mineral Technology for Problem Well Water; The Best Chemical Reduction System for City Water Complete Bacteria and Scale Control," ECOsmarte® Planet Friendly, Inc., http://www.ecosmarte.com/sciencesummary.html, 1994, pp. 1-13.

"Krebs Engineers® Products," 2006 Krebs Engineers, http//www.krebs.com/about.php/ and http://www.krebs.com/products/php/product/20/CycloClean%AE+Modules, 2006, pp. 1-3.

Office Action from the United States Patent and Trademark Office for U.S. Appl. No. 11/655,359, dated Mar. 19, 2009.

Restriction Requirement from the United States Patent and Trademark Office for U.S. Appl. No. 11/655,390, dated Apr. 10, 2009.

Office Action from the United States Patent and Trademark Office for U.S. Appl. No. 11/655,390, dated Jul. 16, 2009.

Office Action from the United States Patent and Trademark Office for U.S. Appl. No. 11/655,359, dated Nov. 13, 2009.

Restriction Requirement from the United States Patent and Trademark Office for U.S. Appl. No. 11/655,385, dated Dec. 9, 2009.

Final Office Action from the United States Patent and Trademark Office for U.S. Appl. No. 11/655,390, dated Jan. 11, 2010.

Office Action from the United States Patent and Trademark Office for U.S. Appl. No. 11/655,378, dated Jan. 14, 2010.

Office Action from the United States Patent and Trademark Office for U.S. Appl. No. 11/655,385, dated Jan. 29, 2010.

WASHING SYSTEMS INCORPORATING CHARGED ACTIVATED LIQUIDS

CROSS-REFERENCE TO RELATED APPLICATIONS

The present application is a continuation-in-part application of U.S. patent application Ser. Nos. 12/639,622 and 12/639,628, each filed on Dec. 16, 2009, and each of which is based on and claims priority to U.S. Provisional Patent Application No. 61/138,465, filed Dec. 17, 2008; and U.S. Provisional Patent Application No. 61/248,557, filed Oct. 5, 2009; the contents of which are hereby incorporated by reference in their entireties.

The present application also is also based on and claims priority to U.S. Provisional Patent Application No. 61/146,903, filed on Jan. 23, 2009, the contents of which are also hereby incorporated by reference in its entirety.

FIELD OF THE DISCLOSURE

The present disclosure relates to washing systems, such as laundry washing machines, dishwashing machines, and sink and faucet-type washing systems. In particular, the present disclosure relates to washing systems that incorporate charged activated liquids.

BACKGROUND

Automated washing system technology has vastly reduced workloads of users for cleaning apparel and articles, such as clothing, dishes, and utensils. Laundry machines are typically provided as top-loading machines or front-loading machines, which designate the orientation of the internal machine tub. Each of these systems clean clothing or other fabrics, for example, with the use of water, detergents, agitation, and if desired, thermal energy.

For example, in a top-loading system, the clothing may be placed in the drum tub along with a chemical detergent. When the washing machine is operated, water is introduced into the drum from a supply line. When a sufficient quantity of water is introduced, the drum rotates the tub in an oscillating manner to allow the chemical detergents to remove dirt, oil, and other contaminants from the clothing. After the wash cycle is complete, a spin cycle may be performed to remove the contaminated water from the tub. A rinse cycle may then be performed to remove any residual contaminated water, followed by one or more additional spins cycle to drain the used water from the tub.

Similarly, in a dishwashing machine, the dishes and utensils retained within the interior of the dishwasher, which is also referred to as a tub, are subjected to washing, rinsing, and drying cycles. The washing cycle typically involves introducing heated water from a supply line, and exposing the dishes and utensils to a detergent. The rinse cycle then removes the contaminated water prior to drying.

Chemical detergents are used in almost all commercial and residential laundry and dishwashing systems. The detergents may include a variety of chemicals, such as surfactants, enzymes, bleaching agents, and phosphates. Such chemicals may undesirably attack the articles being cleaned, which may result in a reduction in the quality of the cleaned articles (e.g., faded and eroded clothing). Furthermore, such chemicals increase contamination in the waste water drained from such washing machines, which increase environmental concerns.

Thus, there is an ongoing need for systems and techniques for cleaning articles with reduced quantities of detergents and reduced volumes of water.

SUMMARY

An aspect of the disclosure is directed to a washing system that includes a washing machine vessel, an electrolysis cell configured to electrochemically activate a received liquid to produce an electrochemically-activated liquid, and an electrode located downstream from the electrolysis cell and configured to be in electrical contact the with electrochemically-activated liquid to produce a charged electrochemically-activated liquid The washing system also includes a dispenser located downstream from the electrolysis cell and downstream or integral with the electrode, where the dispenser is configured to dispense the charged electrochemically-activated liquid into the washing machine vessel. The washing system further includes at least one control circuit configured to generate an electrical field in the electrolysis cell, and further configured to generate an alternating electrical field through the dispensed liquid between the electrode the washing machine vessel.

Another aspect of the disclosure is directed to a washing system that includes a washing machine vessel, a fluid-treatment component operably coupled to a fluid line and configured to activate a liquid received from the fluid line to produce an activated liquid, and an electrode located downstream from the fluid-treatment component and configured to be in electrical contact the with activated liquid to produce a charged activated liquid The washing system also includes a dispenser located downstream from the fluid-treatment component and downstream or integral with the electrode, where the dispenser is configured to dispense the charged activated liquid into the washing machine vessel. The washing system further includes at least one control circuit configured to generate an alternating electrical field through the dispensed liquid between the electrode and the washing machine vessel.

A further aspect of the disclosure is directed to a method for operating a washing system. The method includes activating a liquid to produce an activated liquid, and dispensing the activated liquid from a dispenser of the washing system into a washing system vessel to create an electrically conductive path through the activated liquid from the dispenser to the washing system vessel. During the step of dispensing, the method also includes generating an alternating electrical field through the activated liquid from the dispenser to the washing system vessel.

DETAILED DESCRIPTION

The following is provided as additional description of examples of one or more aspects of the present disclosure. The below detailed description and above-referenced Figures should not to be read as limiting or narrowing the scope of the invention as will be claimed in issued claims. It will be appreciated that other embodiments of the invention covered by one or more of the claims may have structure and function which are different in one or more aspects from the figures and examples discussed herein, and may embody different structures, methods and/or combinations thereof of making or using the invention as claimed in the claims, for example.

Also, the following description is divided into sections with one or more section headings. These sections and headings are provided for ease of reading and are not intended to limit one or more aspects of the disclosure discussed in a particular section and/or section heading with respect to a particular example and/or embodiment from being combined with, applied to, and/or utilized in another particular example, and/or embodiment which is described in another section and/or section heading. Elements, features and other aspects of one or more examples may be combined and/or interchangeable with elements, features and other aspects of one or more other examples described herein.

An aspect of the present disclosure relates to washing systems and methods of operating washing systems with the use of an activated liquid, such as an electrochemically-activated (EA) liquid and/or a chemically-activated liquid, where the activated liquid may include a blend of an alkaline liquid and an acidic liquid, and where the activated liquid also desirably includes an electrical potential for enhanced sanitization properties. As discussed below, the charged activated liquid increases cleaning efficiencies of washing systems compared to a corresponding non-activated liquid. In an example, this allows a reduced concentration of detergents to be used during the washing cycles, or may eliminate the use of detergents.

The reduction or elimination of detergents correspondingly reduces chemical attacks on washed apparel, dishes, and utensils, and may reduce the concentration of chemicals removed in the residual waste liquid. Furthermore, the increased cleaning efficiencies of the charged activated liquid may also reduce the total amount of liquid required for performing washing and/or rinsing cycles. The following discussion of the charged activated liquid is made with reference to water (e.g., charged activated water) with the understanding that the charged activated liquid of the present disclosure may obtained from a variety of different liquids.

Laundry and Dish Washing Systems

Figure 1:
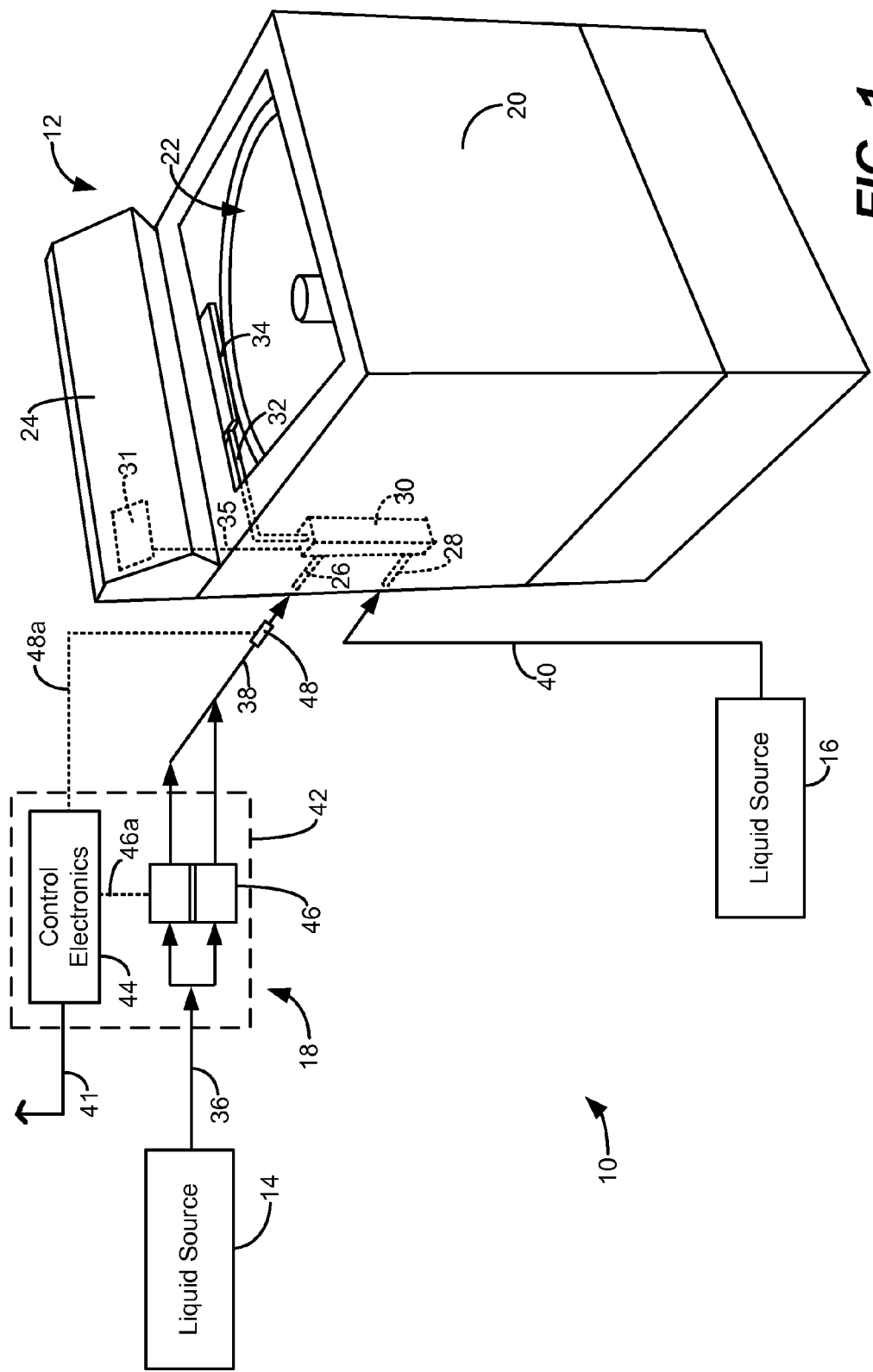
FIG. 1 is a perspective view of a first washing system for performing washing operations with a charged electrochemically-activated liquid, where the washing system includes an external electrolysis unit.

As shown in FIG. 1, washing system 10 includes washing machine 12, liquid sources 14 and 16, and electrolysis unit 18. In this non-limiting example, washing machine 12 is a laundry washing machine for cleaning clothing articles with the use of a first liquid (e.g., hot or cold water) from liquid source 14 and a second liquid (e.g., hot or cold water) from liquid source 16. Washing machine 12 includes machine housing 20, rotary tub 22, control panel 24, liquid inlets 26 and 28, inlet valve unit 30, controller 31, fluid line 32, and dispenser 34, which may be components of a conventional washing machine. Accordingly, machine housing 20 is the exterior housing of washing machine 12, which retains rotary tub 22 and control panel 24.

Rotary tub 22 is desirably a unit configured to receive and retain clothing articles for the cleaning process. In this example, rotary tub 22 is configured as a top-loading tub, but could be configured in other arrangements, such as a front-end loading tub. As discussed below, rotary tube 22 receives charged EA water for use during one or more washing and/or rinsing cycles. Liquid inlets 26 and 28 are openings through machine housing 20 for receiving fluid lines (e.g., fluid hoses), thereby directing the received liquids to inlet valve unit 30. Inlet valve unit 30 is a regulator unit configured to receive and, optionally, combine the liquid streams from liquid sources 14 and 16 (e.g., hot and cold water). Inlet valve unit 30 may then regulate the flow of the combined streams to fluid line 32 based on signals received from controller 31.

Controller 31 is an electronic controller configured to direct the operation of the systems of washing machine 12, such as the rotation of rotary tub 22 and the flow rates through inlet valve unit 30. As shown in FIG. 1, inlet valve unit 30 is in electrical communication with controller 31 via communication line 35. The combined liquid streams may be relayed to dispenser 34 via fluid line 32, where dispenser 34 dispenses the combined liquid streams into rotary tub 22 during washing and rinsing cycles. Washing machine 12 may also include a variety of additional components (not shown) for operation, such as agitator/spin motors and pulley assemblies, liquid pumps, drain lines, filters, and other conventional components.

Liquid sources 14 and 16 may be any suitable supply sources of liquids, such as hot and cold water lines or storage reservoirs. In the shown embodiment, liquid source 12 is connected to electrolysis unit 18 via fluid line 36, and electrolysis unit 18 is correspondingly connected to liquid inlet 26 via fluid line 38. In this embodiment, liquid source 16 may be directly connected to liquid inlet 28 via fluid line 40.

Electrolysis unit 18 is an electrically-powered, fluid-treatment component that may be secured to any suitable location between liquid source 14 and inlet line 26, upstream from washing machine 12. As discussed below, in alternative embodiments, one or more electrolysis units (e.g., electrolysis unit 18) may be located a variety of different locations upstream or downstream from one or more of liquid inlet 26, liquid inlet 28, inlet valve unit 30, fluid line 32, and dispenser 34. As used herein, the term "upstream" and downstream" refer to locations relative to the flow of liquids (e.g., water) through washing systems of the present disclosure (e.g., washing system 10).

In the embodiment shown in FIG. 1, electrolysis unit 18 is an external unit that may be integrated between washing machine 12 and liquid source 14, thereby allowing electrolysis unit 18 to be used with a conventional washing machine and residential or commercial water supply lines. For example, electrolysis unit 18 may be a self-contained unit connectable to a conventional water inlet line of washing machine 12, and may be electrically connected to an external power supply (not shown) via electrical line 41.

Electrolysis unit 18 includes housing 42, control electronics 44, electrolysis cell 46, and electrode 48, where housing 42 may be mounted at any suitable location between washing machine 12 and liquid source 14 for protecting control electronics 44 and electrolysis cell 46 from external conditions. As further shown, fluid line 36 supplies water (e.g., hot or cold water) to inlet lines of electrolysis unit 18, which correspondingly split the received water into a pair of substreams, and direct the substreams to electrolysis cell 46. In another example, the substreams may be split within electrolysis cell 46.

Control electronics 44 direct the operation of electrolysis unit 18, and are configured to relay electrical power from electrical line 41 to electrolysis cell 46 (via electrical line 46a) and to electrode 48 (via electrical line 48a) during operation. For example, in one embodiment, control electronics 44 may be in electrical communication with controller 31 such that controller 31 may direct control electronics 44 to energize and de-energize electrolysis cell 46 and electrode 48 when based on the flow through inlet valve unit 30. In alternative embodiments, control electronics 44 may operate independently from controller 31, such as with a separate actuator that directs control electronics 44 to energize and de-energize electrolysis cell 46 and electrode 48. In additional alternative embodiments, control electronics 4 may be in electrical communication with one or more flow rate monitors (not shown) secured to liquid source 14, fluid line 36, and/or fluid line 38. In these embodiments, the flow rate monitors may detect when water flows through fluid line 36 and/or fluid line 38, thereby allowing control electronics 44 to energize and de-energize electrolysis cell 46 and electrode 48 based on the water flow rate.

Electrolysis cell 46 is a fluid treatment cell that is adapted to apply an electric field across the liquid between at least one anode electrode and at least one cathode electrode. Suitable cells for electrolysis cell 46 may have any suitable number of electrodes, and any suitable number of chambers for containing the water. As discussed below, electrolysis cell 46 may include one or more ion exchange membranes between the anode electrode and the cathode electrode, or can be configured without ion exchange membranes. Electrolysis cell 46 may have a variety of different structures, such as, but not limited to those disclosed in U.S. patent application Ser. Nos. 12/639,622 and 12/639,628. In an alternative embodiment, electrolysis unit 18 may include multiple electrolysis cells 46 that operate in series and/or parallel arrangements to electrochemically activate the water.

As discussed above, the water may be supplied to electrolysis cell 46 through inlet lines, which split the water stream prior to entering electrolysis cell 46. Alternatively, the water may be separated after entering electrolysis cell 46. In alternative embodiments, the water may enter electrolysis cell 46 directly from fluid line 36 as a single stream. As the water flows through electrolysis cell 46, the electric field applied across the water in electrolysis cell 46 electrochemically activates the water, which separates the water by collecting positive ions (i.e., cations, $H^+$) on one side of an electric circuit and collecting negative ions (i.e., anions, $OH^-$) on the opposing side. As discussed below, the water having the cations is thereby rendered acidic and the water having the anions is correspondingly rendered alkaline.

Electrode 48 is an electrical conductor, lead, probe, or other electrical that is positioned along fluid line 38 to electrically contact the EA water flowing through fluid line 38 and to impart, induce or otherwise create an electrical potential in the EA water flowing through fluid line 38 relative to Earth ground, for example. If water exiting dispenser 34, for instance, already carries a charge, such an electrical potential can be a separate or additional electrical potential in the water output, for example.

In the example shown in FIG. 1, electrode 48 is positioned along fluid line 38 and is configured to make electrical contact with the water flowing through fluid line 38. In alternative embodiments, electrode 48 may be located at any position along the water flow path from electrolysis cell 46 to dispenser 34, such as downstream from electrolysis cell 46, and upstream from or incorporated into dispenser 34. For example, electrode 48 may be an integral component of dispenser 34 and electrical line 48a may extend through machine housing 20 to control electronics 44 in electrolysis unit 18. As used herein, the term "integral component", with reference to an electrode being an integral component of a dispenser includes embodiments in which the electrode includes one or more components that are secured to the dispenser, and embodiments in which at least a portion of the electrode is fabricated as a single component with the dispenser. As such, embodiments in which electrode 48 is an integral component of dispenser 34, electrode 48 is configured to make electrical contact with the water flowing through dispenser 38.

Furthermore, the fluid path(s) downstream from electrode 48 are desirably electrically isolated to reduce the extent that the charged EA water is grounded prior to being dispensed from dispenser 34. In the shown embodiment, electrode 48 has no corresponding return electrode of opposite polarity. Further, in other embodiments more than one electrical conductor, lead, or other electrical component or combination thereof may be utilized to impart, induce or otherwise cause an electrical potential to the water.

As discussed below, the electrical potential created and/or supplemented by electrode 48 may be applied to microorganisms on the surface of articles being cleaned with the dispensed water in rotary tub 22. Furthermore, if the charge delivery is of a sufficient magnitude, such a charge can cause irreversible damage, destruction to or otherwise eliminate microorganisms through a mechanism such as electroporation and/or electrohydraulic shock. This enhances sanitization properties of the water dispensed from dispenser 34 during use.

Accordingly, during a washing or rinsing cycle, water is directed from liquid source 14 to electrolysis cell 46 via feed line 36 and the inlet lines of electrolysis unit 18. While flowing through electrolysis cell 46, the liquid is electrochemically activated and provided to fluid line 38 via the outlet lines of electrolysis unit 18. When entering fluid line 38, the resulting streams of the EA liquid are blended together. Despite being blended together, the acidic water and the alkaline water retain their ionic properties and gas-phase bubbles for a sufficient duration to assist in washing and/or rinsing cycles.

Electrode 48 may then impart, induce or otherwise cause an electrical potential in the blended EA water (and/or non-electrolyzed water) flowing through fluid line 38. The resulting charged EA water is then directed to inlet valve unit 30, where the charged EA liquid may combine with water from liquid supply 16 and fluid line 40. For example, liquid sources 14 and 16 may respectively be cold and hot water lines, where the cold water undergoes the electrolysis process in electrolysis unit 18. In an alternative embodiment, liquid source 14 may be a hot water line, and liquid source 16 may be a cold water line, where the hot water undergoes the electrolysis process in electrolysis unit 18.

Inlet valve unit 30 may regulate the relative amounts and flow rates of the separate water streams that are relayed to fluid line 32 and dispenser 34 based on the cycle programming of washing machine 12. For example, in a cold-water washing cycle, controller 31 may direct inlet valve unit 30 to close the line from liquid source 16 and fluid line 40, thereby only allowing the charged EA water to flow to fluid line 32 and dispenser 34. The charged EA water dispensed from dispenser 34 may then be used during the washing cycle to assist in washing the retained clothing articles. As discussed below, the use of the charged EA water increases cleaning efficiencies, thereby allowing a reduction or elimination of detergents, in addition to having sanitation properties. For example, the use of the charged EA water may reduce the number of required washing and/or rinsing cycles. Furthermore, in one embodiment, the use of the charged EA water may eliminate the need of rinsing cycles. This may, for example, allow a single washing cycle to be performed, which may substantially reduce the time and amount of water required to perform a washing operation.

For example, the washing systems of the present disclosure may be used to clean articles with a single wash cycle, and without separate rinse cycles. In this embodiment, the washing operation may be performed without a detergent, where the charged EA water may entrap dirt, oil, and other contaminants from the clothing articles, as discussed above. The contaminated water may then be purged from rotary tub 22 with a spin cycle. Because the washing operation may be performed without a detergent, for example, a separate rinse cycle may not be required. Thus, the charged EA water may only need to be dispensed into rotary tub 22 for a single cycle, thereby reducing the time and amount of water required to wash clothing articles.

Figure 2:
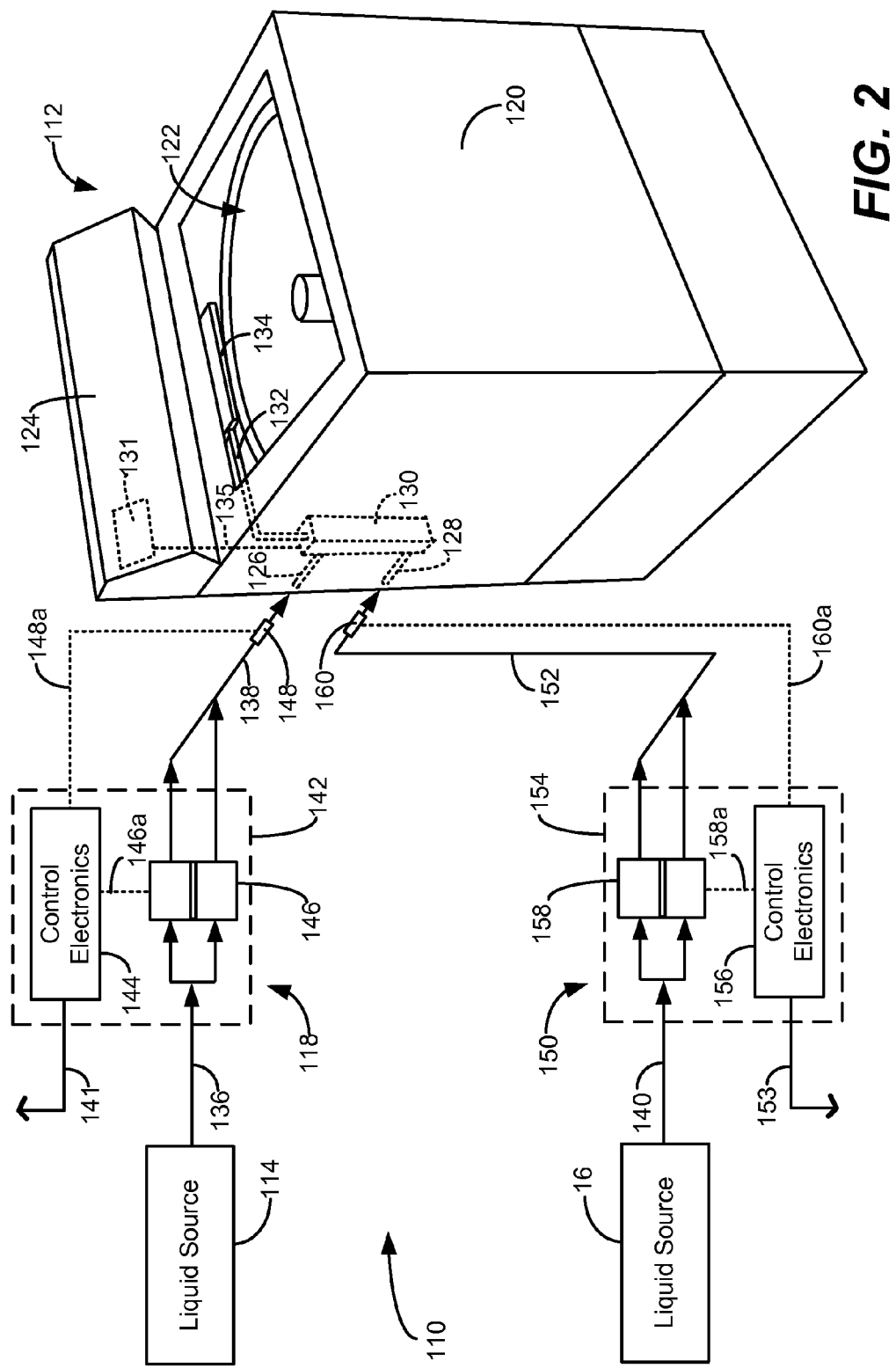
FIG. 2 is a perspective view a second washing system for performing washing operations with a charged electrochemically-activated liquid, where the washing system includes a pair of external electrolysis units.

FIG. 2 illustrates washing system 110, which is a second washing system to washing system 10 (shown in FIG. 1), and where corresponding reference labels are increased by "100". As shown in FIG. 2, washing system 110 further includes electrolysis unit 150 and fluid line 152, where electrolysis unit 150 is a second external electrolysis unit for generating charged EA water from the water of liquid source 116.

Electrolysis unit 150 is also an electrically-powered, fluid-treatment component, and may be secured to any suitable location between liquid source 116 and inlet line 128. For example, electrolysis unit 150 may also be a self-contained unit connectable to a conventional water inlet line of washing machine 112, and may be electrically connected to an external power supply (not shown) via electrical line 153. Electrolysis unit 150 may function in the same manner as electrolysis unit 18 (shown in FIG. 1), and includes housing 154, control electronics 156, electrolysis cell 158, and electrode 160, where housing 154 may be mounted at any suitable location between washing machine 112 and liquid source 116 for protecting control electronics 156 and electrolysis cell 158 from external conditions. As further shown, fluid line 140 supplies water to inlet lines of electrolysis unit 150, which correspondingly split the received water into a pair of substreams, and direct the substreams to electrolysis cell 158. In another example, the substreams may be split within electrolysis cell 158.

Control electronics 156 direct the operation of electrolysis unit 150, and are configured to relay electrical power from electrical line 153 to electrolysis cell 158 (via electrical line 158a) and to electrode 160 (via electrical line 160a) during operation, as discussed above for control electronics 44 (shown in FIG. 1). Electrolysis cell 158 is a fluid treatment cell that is adapted to apply an electric field across the liquid between at least one anode electrode and at least one cathode electrode, and may function in the same manner as discussed above for electrolysis cell 46 (shown in FIG. 1).

Electrode 160 is an electrical conductor, lead, probe, or other electrical contact that is positioned along fluid line 152 to electrically contact the EA water flowing through fluid line 152 and to impart, induce or otherwise create an electrical potential in the EA water flowing through fluid line 152, as discussed above for electrode 48 (shown in FIG. 1). In alternative embodiments, electrode 160 may be located at any position along the water flow path from electrolysis unit 150 to dispenser 134. For example, electrode 160 may be secured to dispenser 134 and electrical line 160a may extend through machine housing 120 to control electronics 156 in electrolysis unit 150. Furthermore, the fluid path(s) downstream from electrode 160 are desirably electrically isolated to reduce the extent that the charged water is grounded prior to being dispensed from dispenser 134. In the shown embodiment, electrode 160 has no corresponding return electrode of opposite polarity. Further, in other embodiments more than one electrical conductor, lead, or other electrical component or combination thereof may be utilized to impart, induce or otherwise cause an electrical potential to the water.

During a wash or rinse cycle, water from liquid source 14 (e.g., cold water) may undergo a first electrolysis process in electrolysis cell 146 to form a first alkaline stream and a first acidic stream. The first alkaline and acidic streams are directed to fluid line 138 via outlet lines of electrolysis unit 118. When entering fluid line 138, the resulting streams of the EA liquid are blended together, as discussed above. Electrode 148 may then impart, induce or otherwise cause an electrical potential in the blended EA water (and/or non-electrolyzed water) flowing through fluid line 138. The resulting charged EA water is then directed to inlet valve unit 130.

Similarly, water from liquid source 16 (e.g., hot water) may undergo a second electrolysis process in electrolysis cell 158 to form a second alkaline stream and a second acidic stream. The second alkaline and acidic streams are directed to fluid line 152 via outlet lines of electrolysis unit 150. When entering fluid line 152, the resulting streams of the EA liquid are blended together, as discussed above. Electrode 160 may then impart, induce or otherwise cause an electrical potential in the blended EA water flowing through fluid line 152. The resulting charged EA water is then directed to inlet valve unit 130.

Inlet valve unit 130 may then combine the first and second charged EA water streams based on signals from controller 131, and may relay the combined charged EA water to fluid line 132 and dispenser 134 for use in the wash or rinse cycle. This arrangement allows the water streams from liquid sources 114 and 116 to selectively undergo electrolysis and charging processes, independent of each other, to generate charged EA water streams.

Figure 3:
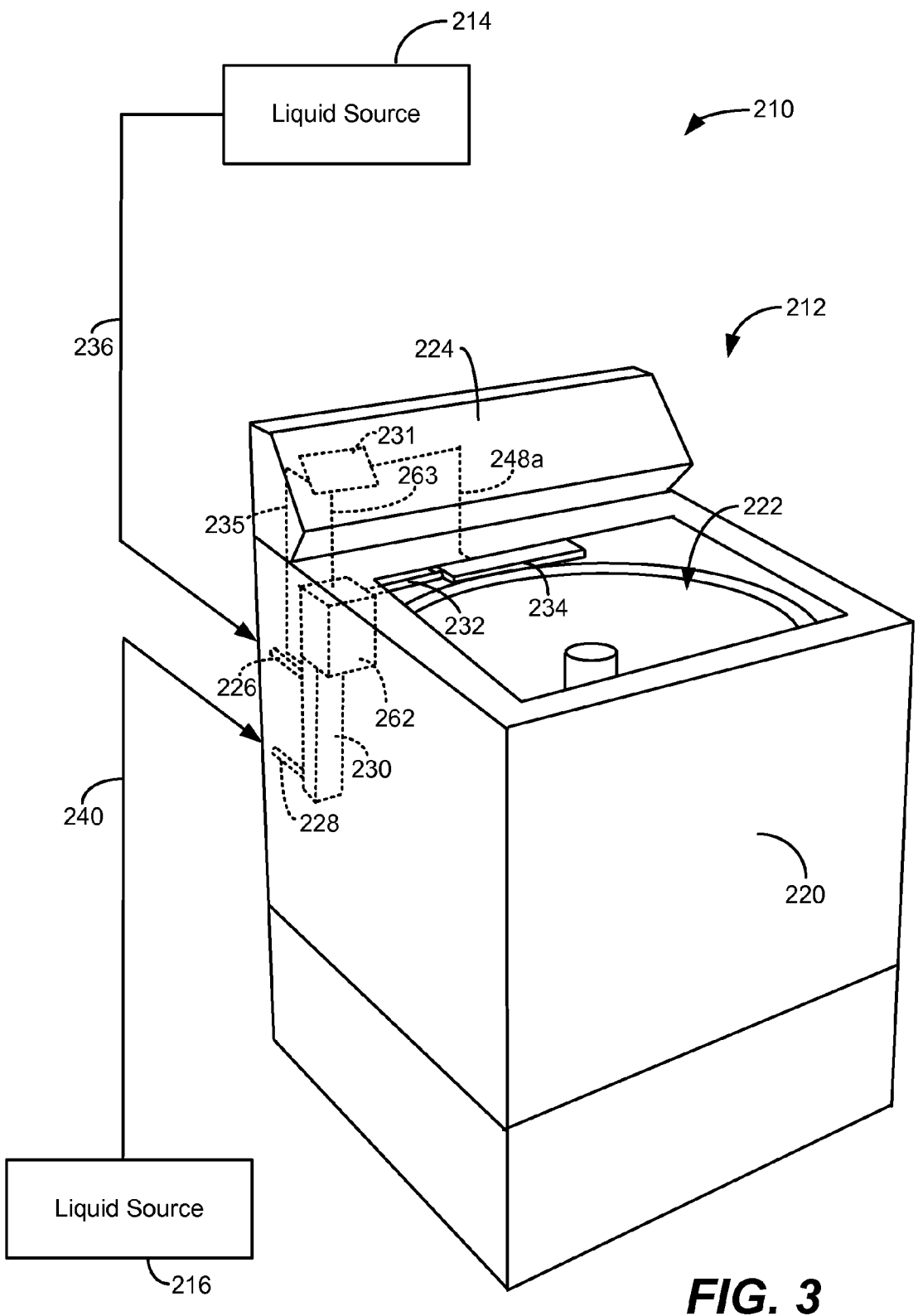
FIG. 3 is a perspective view a third washing system for performing washing operations with a charged electrochemically-activated liquid, where the washing system includes an internal electrolysis unit.

FIG. 3 illustrates washing system 310, which is a third washing system to washing system 10 (shown in FIG. 1), where corresponding reference labels are increased by "200". As shown in FIG. 3, washing system 110 includes electrolysis unit 262 in lieu of (and/or in addition to) electrolysis units 18, 118, and 150. In this embodiment, electrolysis unit 262 may be an internal component of washing machine 212, and is desirably located downstream from inlet valve unit 230. Electrolysis unit 262 may function in the same manner as discussed above for electrolysis unit 18 (shown in FIG. 1).

In comparison to the external electrolysis units 18, 118, and 150, the location of electrolysis unit 262 allows electrolysis unit 262 to generate an EA water stream from the combined hot/cold streams from inlet valve unit 230. This allows the hot and cold water streams to undergo an electrolysis process with a single electrolysis unit. Furthermore, the location of electrolysis unit 262 reduces the residence time of the EA water in transit to dispenser 234. This further preserves the ionic properties and gas-phase bubbles of the resulting EA water stream for a sufficient duration to assist in washing and/or rinsing cycles. In an alternative embodiment, the separation of the alkaline and acidic streams of the EA water may be maintained until entering rotary tub 22.

In one embodiment, electrolysis unit 262 may also be in electrical communication with controller 231 via communication line 263, thereby allowing activation of electrolysis unit 262 to coincide with the operation of inlet valve assembly 230. This electrical communication is beneficial for regulating the operation of electrolysis unit 262 when inlet valve assembly 230 directs the water flow to dispenser 234. For example, controller 231 may be configured to relay electrical power from the power supply (not shown) of washing machine 212 to the electrolysis cell (not shown) of electrolysis unit 262 via line 263 and to the electrode (not shown) of electrolysis unit 262 via line 248a. On one example, the electrode is desirably located as close as possible to, or is incorporated in, dispenser 234. Dispenser 234 is configured to maintain a electrically-conductive pathway along the water flowing through dispenser 234. This arrangement allows the operation of electrolysis unit 262 to coincide with the various stages of the washing and rinsing cycles. The electrode of electrolysis unit 262 is desirably located at fluid line 232 and/or at dispenser 234, thereby reducing the distance that the charged EA water travels prior to being dispensed compared to the embodiments in which the electrodes are secured to fluid lines upstream of washing machine 212 (e.g., as shown in FIGS. 1 and 2).

While the above-discussed washing systems illustrate laundry washing machines for cleaning laundry articles, these systems may also incorporate washing machines for cleaning dishes and utensils in the same manner. For example, while not being required or necessarily preferred, the use of charged EA liquids with dish washing systems may increase drying time efficiencies, reduce heat/energy consumption, and/or reduce water consumption. As discussed above, the use of charged EA liquids (e.g., charged EA water) increases cleaning efficiencies of washing systems, which may reduce or eliminate the use of detergents, and may also reduce the total amount of liquid required for performing washing and/or rinsing cycles.

Electrolysis Units

Figure 4:
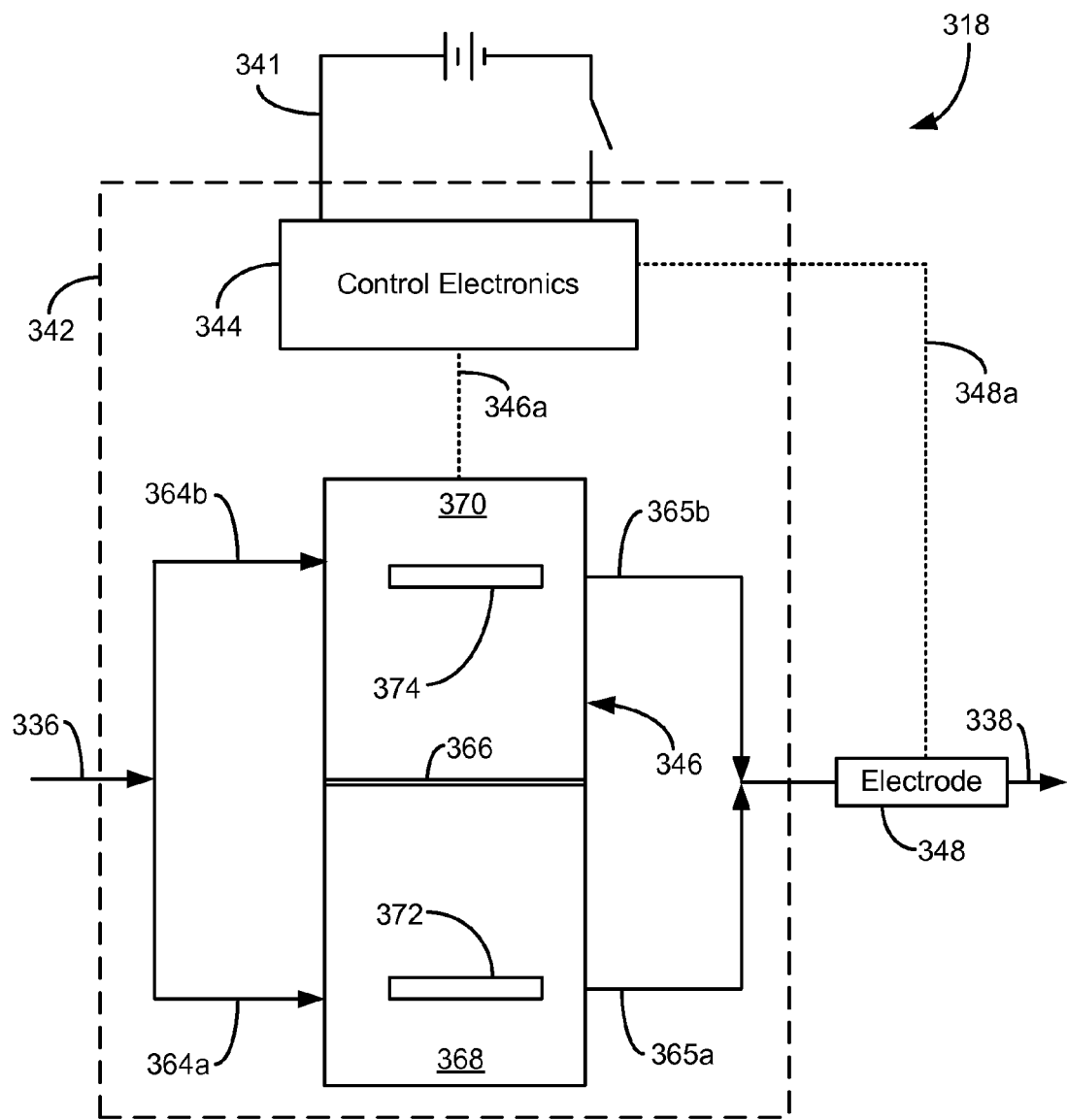
FIG. 4 is a schematic diagram illustrating a first electrolysis unit of a washing system, which includes an electrolysis cell having a dual-chamber arrangement with an ion-exchange membrane.

FIG. 4 is a schematic diagram illustrating electrolysis unit 318, which is a suitable design for electrolysis units 18, 118, and 262, where the corresponding reference labels are increased by "300" from the embodiment shown in FIG. 1. As shown in FIG. 4, electrolysis unit 318 includes inlet lines 364a and 364b, and outlet lines 365a and 365b. Electrolysis cell 346 further includes membrane 366, which separates electrolysis cell 346 into anode chamber 368 and cathode chamber 370. While electrolysis cell 346 is illustrated in FIG. 4 as having a single anode chamber and a single cathode chamber, electrolysis cell 346 may alternatively include a plurality of anode and cathode chambers separated by one or more membranes 366.

Membrane 366 is an ion exchange membrane, such as a cation exchange membrane (i.e., a proton exchange membrane) or an anion exchange membrane. Suitable cation exchange membranes for membrane 366 include partially and fully fluorinated ionomers, polyaromatic ionomers, and combinations thereof. Examples of suitable commercially available ionomers for membrane 366 include sulfonated tetrafluoroethylene copolymers available under the trademark "NAFION" from E.I. du Pont de Nemours and Company, Wilmington, Del.; perfluorinated carboxylic acid ionomers available under the trademark "FLEMION" from Asahi Glass Co., Ltd., Japan; perfluorinated sulfonic acid ionomers available under the trademark "ACIPLEX" Aciplex from Asahi Chemical Industries Co. Ltd., Japan; and combinations thereof. Other examples of suitable membranes include those available from Membranes International Inc. of Glen Rock, N.J., such as the CMI-7000S cation exchange membrane and the AMI-7001S anion exchange membrane.

Anode chamber 368 and cathode chamber 370 respectively include anode electrode 372 and cathode electrode 374, where membrane 366 is disposed between anode electrode 372 and cathode electrode 374. Anode electrode 372 and cathode electrode 374 can be made from any suitable electrically-conductive material, such as stainless steel and/or titanium, and may be coated with one or more precious metals (e.g., platinum). In one embodiment, anode electrode 372 and/or cathode electrode 374 are at least partially or wholly made from a conductive polymer.

Anode electrode 372 and cathode electrode 374 may each also exhibit a variety of different geometric designs and constructions, such as flat plates, coaxial plates (e.g., for tubular electrolytic cells), rods, and combinations thereof; and may have solid constructions or can have one or more apertures (e.g., metallic meshes). While anode chamber 368 and cathode chamber 370 are each illustrated with a single anode electrode 372 and cathode electrode 374, anode chamber 368 may include a plurality of anode electrodes 372, and cathode chamber 370 may include a plurality of cathode electrodes 374.

Anode electrode 372 and cathode electrode 374 may be electrically connected to opposing terminals of electrical line 346a, thereby allowing anode electrode 372 and cathode electrode 374 to operably receive electrical power from a power supply via electrical line 241 and control electronics 344. The power supply can provide electrolysis cell 346 with a constant direct-current (DC) output voltage, a pulsed or otherwise modulated DC output voltage, an AC output voltage, and/or a pulsed or otherwise modulated AC output voltage, to anode electrode 372 and cathode electrode 374. The power supply can have any suitable output voltage level, current level, duty cycle, or waveform.

In one embodiment, the power supply and/or control electronics 344 applies the voltage supplied to anode electrode 372 and cathode electrode 374 at a relative steady state. Additionally, the power supply may include a DC/DC converter that uses a pulse-width modulation (PWM) control scheme to control voltage and current output. Other types of power supplies can also be used, which can be pulsed or not pulsed, and at other voltage and power ranges. The parameters may vary depending on a specific application and/or embodiment.

During operation, water may be supplied to electrolysis cell 346 from inlet lines 364a and 364b, which are the separated pathways of fluid line 336. The water flowing through inlet line 364a flows into anode chamber 368, and the water flowing through inlet line 364b flows into cathode chamber 370. A voltage potential is applied to electrochemically activate the water flowing through anode chamber 368 and cathode chamber 370.

For example, in an embodiment in which membrane 366 is a cation exchange membrane, upon application of a DC voltage potential across anode electrode 372 and cathode electrode 374, such as a voltage in a range of about 5 volts to about 28 volts, or for example about 5 volts to about 38 volts, cations originally present in anode chamber 368 move across the membrane 366 towards cathode electrode 374 while anions in anode chamber 368 move towards anode electrode 372. However, anions present in cathode chamber 370 are not able to pass through membrane 366, and therefore remain confined within cathode chamber 370.

As a result, electrolysis cell 346 can electrochemically activate the water by at least partially utilizing electrolysis, and may produce EA water in the form of an acidic anolyte stream (e.g., through outlet line 365a) and a basic catholyte stream (e.g., through outlet line 365b). In one example, the anolyte stream has an oxidation-reduction potential (ORP) of at least about +50 millivolts (mV) (e.g., in a range of +50 mV to +1200 mV), and the catholyte stream has an ORP of at least about −50 mV (e.g., in a range of −50 mV to −1000 mV).

If desired, the anolyte and catholyte streams can be generated in different ratios to one another through modifications to the structure of electrolysis cell 346. For example, electrolysis cell 346 can be configured to produce a greater volume of the catholyte stream relative to the anolyte stream if the primary function of the EA water is cleaning. Alternatively, for example, electrolysis cell 346 can be configured to produce a greater volume of anolyte stream relative to the catholyte stream if the primary function of the EA water is sanitizing.

Also, the concentrations of reactive species in each can be varied. For example, electrolysis cell 346 can have a 3:2 surface-area ratio of cathode electrode 374 to anode electrode 372 for producing a greater volume of the catholyte stream relative to the anolyte stream (e.g., about 60% catholyte to about 40% anolyte). Also, the duty cycle of the applied voltage and/or other electrical characteristics can be modified to modify the relative amounts of catholyte and anolyte streams produced by electrolysis cell 346.

The ability to produce a large voltage and a suitable current through electrolysis cell 346 can be beneficial for applications in which regular tap water is fed through electrolysis cell 346 to be converted into EA water having enhanced cleaning and/or sanitizing properties. Regular tap water has a relatively low electrical conductivity between anode electrode 372 and cathode electrode 374. In one example, control electronics 344 may output a voltage that is controlled to achieve a current draw through electrolysis cell 346 that is within a predetermined current range, such as with a DC-to-DC converter. For example, the target current draw is about 400 milliamperes. In another example, the target current is 350 milliamperes. Other currents and ranges can be used in alternative embodiments. The desired current draw may depend on the geometry of electrolysis cell 346, the properties of the liquid being treated, the flow rate of the liquid, and the desired properties of the resulting electrochemical reaction.

As discussed in U.S. patent application Ser. Nos. 12/639,622 and 12/639,628, in some embodiments, control electronics 344 may apply a substantially constant, relatively positive voltage to anode electrode 372, and a substantially constant, relatively negative voltage applied cathode electrode 374. However, periodically each voltage may be briefly pulsed to a relatively opposite polarity to repel scale deposits. In some examples, there is a desire to limit scale deposits from building on the electrode surfaces. In these examples, during first time periods, a relatively positive voltage may be applied to anode electrode 372 and a relatively negative voltage may be applied to cathode electrode 374, and during second time periods, the voltage applied to each electrode may be reversed. The reversed voltage level can have the same magnitude as the non-reversed voltage level or can have a different magnitude if desired.

The frequency of each brief polarity switch may also be selected as desired. As the frequency of reversal increases, the amount of scaling decreases. However, the electrodes may lose small amounts of platinum (in the case of platinum coated electrodes) with each reversal. As the frequency of reversals decreases, scaling may increase. In one example, the time period between reversals, is in the range of about 1 second to about 600 seconds. Other periods outside this range can also be used. In another example, the time period of normal polarity, is at least 900 milliseconds. The time period at which the voltages are reversed can also be selected as desired. In one example, the reversal time period, is in the range of about 50 milliseconds to about 100 milliseconds. Other periods outside this range can also be used.

With these ranges, for example, anode chamber 368 may produce a substantially constant anolyte EA water output, and cathode chamber 370 may produce a substantially constant catholyte EA water output without requiring valving. In prior art electrolysis systems, complicated and expensive valving is used to maintain constant anolyte and catholyte streams through respective outlets while still allowing the polarity to be reversed to minimize scaling.

If the number of anode electrodes is different than the number of cathode electrodes, e.g., a ratio of 3:2, or if the surface area of anode electrode 372 is different than the surface area of cathode electrode 374, then the applied voltage pattern can be used in the above-discussed manner to produce a greater amount of either anolyte or catholyte in the produced EA water.

It has been found that such frequent, brief polarity reversals for de-scaling the electrodes may have a tendency also to shed materials often used for plating the electrodes, such as platinum, from the electrode surface. Thus in one embodiment, anode electrode 372 and cathode electrode 374 may comprise unplated electrodes, such as metallic electrodes or conductive plastic electrodes. For example, the electrodes can be unplated metallic mesh electrodes.

In one exemplary embodiment, control electronics 344 can further include a switch that can be used to selectively invert the waveform applied to electrolysis cell 346. For example, the switch can be set in one position to generate more anolyte than catholyte and in another position to generate more catholyte than anolyte. Control electronics 344 may monitor the switch position and adjusts the voltage applied to electrolysis cell 346 according to the switch position. However, the electrodes of electrolysis cell 346 can be driven with a variety of different voltage and current patterns, depending on the particular application of electrolysis cell 346.

In another example, the electrodes may be driven at one polarity for a specified period of time (e.g., about 5 seconds) and then driven at the reverse polarity for approximately the same period of time. Since the anolyte and catholyte EA waters are blended at the outlet of electrolysis cell 346, this process produces essentially one part anolyte EA water to one part catholyte EA water. In yet another example, the cell electrodes may be driven with a pulsed DC voltage waveform, where the polarity applied to the electrodes is not reversed. The "on/off" time periods and applied voltage levels can be set as desired.

While not intending to be bound by theory, it is believed that water molecules in contact with anode electrode 372 are electrochemically oxidized to oxygen ($O_2$) and hydrogen ions ($H^+$) in anode chamber 368 while water molecules in contact with the cathode electrode 374 are electrochemically reduced to hydrogen gas ($H_2$) and hydroxyl ions ($OH^-$) in the cathode chamber 370. The hydrogen ions in the anode chamber 368 are allowed to pass through membrane 366 into cathode chamber 370 where the hydrogen ions are reduced to hydrogen gas while the oxygen gas in anode chamber 368 oxygenates the feed water to form the anolyte stream in outlet line 365*a*. Furthermore, since regular tap water typically includes sodium chloride and/or other chlorides, anode electrode 372 oxidizes the chlorides present to form chlorine gas. As a result, a substantial amount of chlorine may be produced and the pH of the anolyte stream in outlet line 365*a* may become increasingly acidic over time.

As noted, water molecules in contact with cathode electrode 374 are electrochemically reduced to hydrogen gas and hydroxyl ions ($OH^-$) while cations in anode chamber 368 pass through membrane 366 into cathode chamber 370 when the voltage potential is applied. These cations are available to ionically associate with the hydroxyl ions produced at cathode electrode 374, while hydrogen gas bubbles form in the liquid. A substantial amount of hydroxyl ions may accumulate over time in cathode chamber 370 and react with cations to form basic hydroxides. In addition, the hydroxides may remain confined to cathode chamber 370 since membrane 366 (as a cation-exchange membrane) does not allow the negatively charged hydroxyl ions pass through. Consequently, a substantial amount of hydroxides may be produced in cathode chamber 370, and the pH of the catholyte stream in outlet line 365*b* may become increasingly alkaline over time.

The electrolysis process in electrolysis cell 346 allows the concentration of reactive species and the formation of metastable ions and radicals to occur in anode chamber 368 and cathode chamber 370. The electrochemical activation process typically occurs by either e.g. electron withdrawal (at anode electrode 372) or electron introduction (at cathode electrode 374), which leads to alteration of physiochemical (including structural, energetic and catalytic) properties of the feed water. It is believed that the feed water (anolyte or catholyte) gets activated in the immediate proximity of the electrode surface where the electric field intensity can reach a very high level. This area can be referred to as an electric double layer (EDL).

While the electrochemical activation process continues, the water dipoles generally align with the field, and a proportion of the hydrogen bonds of the water molecules consequentially break. Furthermore, singly-linked hydrogen atoms may bind to the metal atoms (e.g., platinum atoms) at cathode electrode 374, and single-linked oxygen atoms may bind to the metal atoms (e.g., platinum atoms) at the anode electrode 372. These bound atoms diffuse around in two dimensions on the surfaces of the respective electrodes until they take part in further reactions. Other atoms and polyatomic groups may also bind similarly to the surfaces of anode electrode 372 and cathode electrode 374, and may also subsequently undergo reactions. Molecules such as oxygen ($O_2$) and hydrogen ($H_2$) produced at the surfaces may enter small cavities in the liquid phase of the water (e.g., bubbles) as gases and/or may become solvated by the liquid phase of the water. These gas-phase bubbles are thereby dispersed or otherwise suspended throughout the liquid phase of the water.

The sizes of the gas-phase bubbles may vary depending on a variety of factors, such as the pressure applied to the feed water, the composition of the salts and other compounds in the feed water, and the extent of the electrochemical activation. Accordingly, the gas-phase bubbles may have a variety of different sizes, including, but not limited to macrobubbles, microbubbles, nanobubbles, and/or mixtures thereof. In embodiments including macrobubbles, examples of suitable average bubble diameters for the generated bubbles include diameters ranging from about 500 micrometers to about one millimeter. In embodiments including microbubbles, examples of suitable average bubble diameters for the generated bubbles include diameters ranging from about one micrometer to less than about 500 micrometers. In embodiments including nanobubbles, examples of suitable average bubble diameters for the generated bubbles include diameters less than about one micrometer, with particularly suitable average bubble diameters including diameters less than about 500 nanometers, and with even more particularly suitable average bubble diameters including diameters less than about 100 nanometers.

Surface tension at a gas-liquid interface is produced by the attraction between the molecules being directed away from the surfaces of anode electrode 372 and cathode electrode 374 as the surface molecules are more attracted to the molecules within the water than they are to molecules of the gas at the electrode surfaces. In contrast, molecules of the bulk of the water are equally attracted in all directions. Thus, in order to increase the possible interaction energy, surface tension causes the molecules at the electrode surfaces to enter the bulk of the water.

In the embodiments in which gas-phase nanobubbles are generated, the gas contained in the nanobubbles (i.e., bubbles having diameters of less than about one micrometer) are also believed to be stable for substantial durations in the liquid phase water, despite their small diameters. While not wishing to be bound by theory, it is believed that the surface tension of the water, at the gas/liquid interface, drops when curved surfaces of the gas bubbles approach molecular dimensions. This reduces the natural tendency of the nanobubbles to dissipate.

Furthermore, nanobubble gas/liquid interface is charged due to the voltage potential applied across membrane 366. The charge introduces an opposing force to the surface tension, which also slows or prevents the dissipation of the nanobubbles. The presence of like charges at the interface reduces the apparent surface tension, with charge repulsion acting in the opposite direction to surface minimization due to surface tension. Any effect may be increased by the presence of additional charged materials that favor the gas/liquid interface.

The natural state of the gas/liquid interfaces appears to be negative. Other ions with low surface charge density and/or high polarizability (such as $Cl^-$, $ClO^-$, $HO_2^-$, and $O_2^-$) also favor the gas/liquid interfaces, as do hydrated electrons. Aqueous radicals also prefer to reside at such interfaces. Thus, it is believed that the nanobubbles present in the catholyte (i.e., the sub-stream flowing through cathode chamber 370) are negatively charged, but those in the anolyte (i.e., the sub-stream flowing through anode chamber 368) will possess little charge (the excess cations cancelling out the natural negative charge). Accordingly, catholyte nanobubbles are not likely to lose their charge on mixing with the anolyte sub-stream at the convergence point of fluid line 338.

Additionally, gas molecules may become charged within the nanobubbles (such as $O_2^-$), due to the excess potential on cathode electrode 374, thereby increasing the overall charge of the nanobubbles. The surface tension at the gas/liquid interface of charged nanobubbles can be reduced relative to uncharged nanobubbles, and their sizes stabilized. This can be qualitatively appreciated as surface tension causes surfaces to be minimized, whereas charged surfaces tend to expand to minimize repulsions between similar charges. Raised temperature at the electrode surface, due to the excess power loss over that required for the electrolysis, may also increase nanobubble formation by reducing local gas solubility.

As the repulsion force between like charges increases inversely as the square of their distances apart, there is an increasing outwards pressure as a bubble diameter decreases. The effect of the charges is to reduce the effect of the surface tension, and the surface tension tends to reduce the surface whereas the surface charge tends to expand it. Thus, equilibrium is reached when these opposing forces are equal. For example, assuming the surface charge density on the inner surface of a gas bubble (radius r) is $\Phi(e^-/meter^2)$, the outwards pressure ("$P_{out}$"), can be found by solving the Navier-Stokes equations to give:

$$P_{out} = \Phi^2 / 2D\epsilon_0 \qquad \text{(Equation 1)}$$

where "D" is the relative dielectric constant of the gas bubble (assumed unity), "$\epsilon_0$" is the permittivity of a vacuum (i.e., 8.854 pF/meter). The inwards pressure ("$P_{in}$") due to the surface tension on the gas is:

$$P_{in} = 2g/rP_{out} \qquad \text{(Equation 2)}$$

where "g" is the surface tension (0.07198 Joules/meter$^2$ at 25° C.). Therefore if these pressures are equal, the radius of the gas bubble is:

$$r = 0.28792\epsilon_0/\Phi^2 \qquad \text{(Equation 3)}$$

Accordingly, for nanobubble diameters of 5 nanometers, 10 nanometers, 20 nanometers, 50 nanometers, and 100 nanometers the calculated charge density for zero excess internal pressure is 0.20, 0.14, 0.10, 0.06 and 0.04 $e^-$/nanometer$^2$ bubble surface area, respectively. Such charge densities are readily achievable with the use of electrolysis cell 346. The nanobubble radius increases as the total charge on the bubble increases to the power ⅔. Under these circumstances at equilibrium, the effective surface tension of the water at the nanobubble surface is zero, and the presence of charged gas in the bubble increases the size of the stable nanobubble. Further reduction in the bubble size would not be indicated as it would cause the reduction of the internal pressure to fall below atmospheric pressure.

In various situations within electrolysis cell 346, the nanobubbles may divide into even smaller bubbles due to the surface charges. For example, assuming that a bubble of radius "r" and total charge "q" divides into two bubbles of shared volume and charge (radius $r_{1/2} = r/2^{1/3}$, and charge $q_{1/2} = q/2$), and ignoring the Coulomb interaction between the bubbles, calculation of the change in energy due to surface tension ($\Delta E_{ST}$) and surface charge ($\Delta E_q$) gives:

$$\Delta E_{ST} = +2(4\pi\gamma r_{1/2}^2) - 4\pi\gamma r^2 = 4\pi\gamma r^2(2^{1/3} - 1) \qquad \text{(Equation 4)}$$

and $$\Delta E_q = \qquad \text{(Equation 5)}$$
$$-2\left[1/2 \times \frac{\left[\frac{q}{2}\right]}{4\pi\epsilon_0 r_{1/2}}\right] - 1/2 \times \frac{q^2}{4\pi\epsilon_0 r} = \frac{q^2}{8\pi\epsilon_0 r}[1 - 2^{-2/3}]$$

The bubble is metastable if the overall energy change is negative which occurs when $\Delta E_{ST} + \Delta E_q$ is negative, thereby providing:

$$\frac{q^2}{8\pi\epsilon_0 r}[1 - 2^{-2/3}] + 4\pi\gamma r^2[2^{1/3} - 1] \leq 0 \qquad \text{(Equation 6)}$$

which provides the relationship between the radius and the charge density ($\Phi$):

$$\Phi = \frac{1}{4\pi r^2} \geq \sqrt{\frac{2\gamma\epsilon_0}{r} \frac{[2^{1/3} - 1]}{[1 - 2^{-2/3}]}} \qquad \text{(Equation 7)}$$

Accordingly, for nanobubble diameters of 5 nanometers, 10 nanometers, 20 nanometers, 50 nanometers, and 100 nanometers the calculated charge density for bubble splitting 0.12, 0.08, 0.06, 0.04 and 0.03 $e^-$/nanometer$^2$ bubble surface area, respectively. For the same surface charge density, the bubble diameter is typically about three times larger for reducing the apparent surface tension to zero than for splitting the bubble in two. Thus, the nanobubbles will generally not divide unless there is a further energy input.

Furthermore, the presence of nanobubbles on the surface of particles increases the pickup of the particle by micron-sized gas-phase bubbles, which may also be generated during the electrochemical activation process. The presence of surface nanobubbles also reduces the size of the dirt particle that can be picked up by this action. Such pickup assist in the removal of the dirt particles from articles and prevents re-deposition. Moreover, due to the large gas/liquid surface area-to-volume ratios that are attained with gas-phase nanobubbles, water molecules located at this interface are held by fewer hydrogen bonds, as recognized by water's high surface tension. Due to this reduction in hydrogen bonding to other water molecules, this interface water is more reactive than normal water and will hydrogen bond to other molecules more rapidly, thereby showing faster hydration.

For example, at 100% efficiency a current of one ampere is sufficient to produce 0.5/96,485.3 moles of hydrogen ($H_2$) per second, which equates to 5.18 micromoles of hydrogen per second, which correspondingly equates to 5.18×22.429 microliters of gas-phase hydrogen per second at a temperature of 0° C. and a pressure of one atmosphere. This also equates to 125 microliters of gas-phase hydrogen per second at a temperature of 20° C. and a pressure of one atmosphere. As the partial pressure of hydrogen in the atmosphere is effectively zero, the equilibrium solubility of hydrogen in the electrolyzed solution is also effectively zero and the hydrogen is held in gas cavities (e.g., macrobubbles, microbubbles, and/or nanobubbles).

Assuming the flow rate of the electrolyzed solution is 0.12 U.S. gallons per minute, there is 7.571 milliliters of water flowing through the electrolysis cell each second. Therefore, there are 0.125/7.571 liters of gas-phase hydrogen within the bubbles contained in each liter of electrolyzed solution at a temperature of 20° C. and a pressure of one atmosphere. This equates to 0.0165 liters of gas-phase hydrogen per liter of solution less any of gas-phase hydrogen that escapes from the liquid surface and any that dissolves to supersaturate the solution.

The volume of a 10 nanometer-diameter nanobubble is $5.24 \times 10^{-22}$ liters, which, on binding to a hydrophobic surface covers about $1.25 \times 10^{-16}$ square meters. Thus, in each liter of solution there would be a maximum of about $3 \times 10^{-19}$ bubbles (at 20° C. and one atmosphere) with combined surface covering potential of about 4000 square meters. Assuming a surface layer just one molecule thick, for example, this provides a concentration of active surface water molecules of over 50 millimoles. While this concentration represents an exemplary maximum amount, even if the nanobubbles have greater volume and greater internal pressure, the potential for surface covering remains large. Furthermore, only a small percentage of the dirt particles surfaces need to be covered by the nanobubbles for the nanobubbles to have a cleaning effect.

Accordingly, the gas-phase nanobubbles, generated during the electrochemical activation process in electrolysis cell 346, are beneficial for attaching to dirt particles so transferring their charge. The resulting charged and coated dirt particles are more readily separated one from another due to the repulsion between their similar charges. They will enter the solution to form a colloidal suspension. Furthermore, the charges at the gas/water interfaces oppose the surface tension, thereby reducing its effect and the consequent contact angles. Also, the nanobubbles coating of the dirt particles promotes the pickup of larger buoyant gas-phase macrobubbles and microbubbles that are introduced. In addition, the large surface area of the nanobubbles provides significant amounts of higher reactive water, which is capable of the more rapid hydration of suitable molecules.

The EA water, containing the gas-phase bubbles (e.g., macrobubbles, microbubbles, and nanobubbles), exits electrolysis cell 346 via outlet lines 365a and 365b, and the sub-streams may re-converge at fluid line 338. Although the anolyte and catholyte streams may be blended prior to use in the washing or rinsing cycle, they are initially not in equilibrium and temporarily retain their electrochemically-activated states. As discussed above, in alternative embodiments, the anolyte and catholyte streams may be separated until being dispensed into rotary tub 22. Accordingly, the EA water contains gas-phase bubbles dispersed/suspended in the liquid-phase water. This may reduce the amount of water required during a washing or rinsing cycle, and may also reduce the number of cycles required to perform the washing operation.

Figure 5:
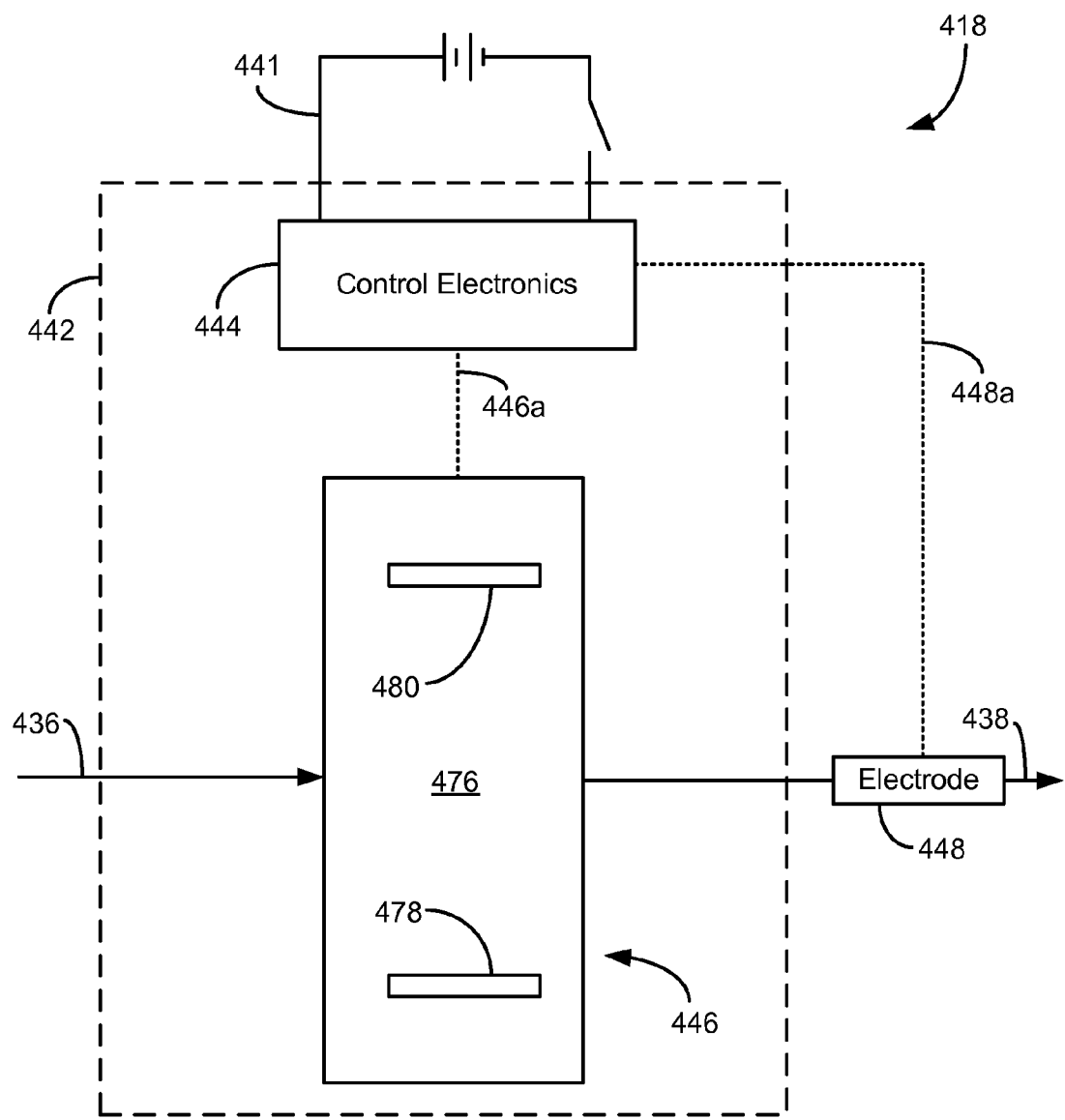
FIG. 5 is a schematic diagram illustrating second electrolysis unit of a washing system, which includes an electrolysis cell having a single-chamber arrangement without an ion-exchange membrane.

FIG. 5 is a schematic diagram illustrating electrolysis unit 418, which is an example of an alternative to electrolysis cell 318 (shown in FIG. 2) for electrochemically activating the water flowing through fluid line 436, without the use of an ion exchange membrane. Electrolysis unit 418 is also a suitable alternative design for electrolysis unit 18 (shown in FIG. 1), electrolysis units 118 and 150 (shown in FIG. 2), and electrolysis unit 262 (shown in FIG. 3) for electrochemically activating water for use in washing systems.

As shown in FIG. 5, electrolysis unit includes electrolysis cell 446, which may engage directly with fluid lines 436 and 438, and includes reaction chamber 476, anode electrode 478, and cathode electrode 480. Reaction chamber 476 can be defined by the walls of electrolysis cell 446, by the walls of a container or conduit in which anode electrode 478 and cathode electrode 480 are placed, or by anode electrode 478 and cathode electrode 480 themselves. Suitable materials and constructions for anode electrode 478 and cathode electrode 480 include those discussed above for anode electrode 372 and cathode electrode 374 (shown in FIG. 4).

During operation, water is introduced into reaction chamber 476 via feed line 436, and a voltage potential is applied across anode electrode 478 and cathode electrode 480. This electrochemically activates the water, where portions of the water near or in contact with anode electrode 478 and cathode electrode 480 generate gas-phase bubbles in the same manner as discussed above for electrolysis cell 346. Thus, the water flowing through electrolysis cell 446 contains gas-phase bubbles dispersed or otherwise suspended in the liquid-phase water. In comparison to electrolysis cell 346, however, the EA water is blended during the entire electrolysis process, rather than being split upstream from, or within, the electrolysis cell, and then re-converged, or within, downstream from the electrolysis cell. Accordingly, the resulting EA water contains gas-phase bubbles dispersed/suspended in the liquid-phase water, which increases the cleaning efficiencies of the liquid, as discussed above.

Alternative Suspension Mechanisms

In alternative embodiments, microorganism suspension can be accomplished through mechanisms other than EA liquids produced by fluid-treatment components such as electrolysis cells (e.g., electrolysis cell 346 and 446). Particular examples of other suspension mechanisms include, for example, any mechanism that alters the ORP of the dispensed water (producing dispensed water having a positive ORP, a negative ORP or a combination of both). For example, it has been found that regular tap water may be altered to have a negative ORP (such as but not limited to −50 millivolts to −600 millivolts) which has enhanced cleaning effects. These enhanced cleaning effects can serve to suspend microorganisms above the surface within the dispensed water, for example. Although negative (and/or positive) ORP can be achieved through an electrolysis cell as described herein, it can also be achieved by other mechanisms such as by passing the water to be dispensed through a filter or other mechanism containing materials, such as zeolites, that alter the ORP of the water.

For example, in one embodiment, electrolysis units 18, 118, 150, 262, 318, and/or 418 may be replaced with one or more media containers, which are fluid-treatment components containing media that compositionally include one or more liquid-activating materials for altering the ORP of the water flowing through fluid lines (e.g., fluid lines 336 and 338 shown in FIG. 3, and fluid lines 436 and 438 shown in FIG. 4). Examples of suitable media cartridges for use with the washing systems of the present disclosure include those disclosed in U.S. patent application Ser. Nos. 12/639,622 and 12/639,628.

Examples of suitable liquid-activating materials for use in the media include porous minerals, such as porous aluminosilicate minerals (e.g., zeolites). Examples of suitable zeolites for use in the media include hydrated and anhydrous structures of aluminosilicate minerals, which may contain one or more of sodium (Na), potassium (K), cerium (Ce), calcium (Ca), barium (Ba), strontium (Sr), lithium (Li), and magnesium (Mg). Examples of suitable zeolites for use in media 1818 include analcime, amicite, barrerite, bellbergite, bikitaite, boggsite, brewsterite, chabazite, clinoptilolite, cowlesite, dachiardite, edingtonite, epistilbite, erionite, faujasite, ferrierite, garronite, gismondine, gobbinsite, gmelinite, gonnardite, goosecreekite, harmotome, heulandite, laumontite, levyne, mazzite, merlinoite, montesommaite, mordenite, mesolite, natrolite, offretite, paranatrolite, paulingite, perlialite, phillipsite, pollucite, scolecite, stellerite, stilbite, thomsonite, tschernichite, wairakite, wellsite, willhendersonite, yugawaralite, anhydrous forms thereof, and combinations thereof. Examples of commercially available zeolites for use in the media include clinoptilolites from KMI Zeolite, Inc., Sandy Valley, Nev., which have an average density of about 2.3 grams/cubic-centimeter and a nominal particle sizing of +40 mesh.

Non-zeolite materials or mechanisms may also be utilized. Examples of suitable non-zeolite minerals for use in the media include resins, apophyllite, gyrolite, hsianghualite, kehoeite, lovdarite, maricopaite, okenite, pahasapaite, partheite, prehnite, roggianite, tacharanite, tiptopite, tobermorite, viseite, and combinations thereof. Examples of suitable resins include ion-exchange resins, such as those having cross-linked aromatic structures (e.g., cross-linked polystyrene) containing active groups (e.g., sulfonic acid groups, amino groups, carboxylic acid groups, and the like). The ion-exchange resins may be provided in a variety of media, such as in resin beads, for example. These non-zeolite minerals may be used in combination with or as alternatives to the zeolites in the media.

The media may be provided in a variety of media forms, such as in ceramic balls, pellets, powders, and the like. While retained in the media cartridge, the media treats the water flowing through the media cartridge between the fluid lines (e.g., fluid lines 336 and 338, and fluid lines 436 and 438), thereby imparting a negative ORP (and/or a positive ORP) on the water by ion exchange, for example. The media desirably imparts a negative ORP to the water of at least about of −50 mV and/or a positive ORP of at least about +50 mV. In another example, the media desirably imparts a negative ORP to the water of at least about of −100 mV and/or a positive ORP of at least about +100 mV. As discussed above, altering the ORP allows the dispensed EA water to suspend particles and microorganisms, as discussed above for electrolysis cells 346 and 446.

Electroporation Electrodes

As discussed above, the electroporation electrodes of the present disclosure (e.g., electrodes 48, 148, 160, 348, and 448) are electrical conductors, leads, probes, or other electrical contacts that impart, induce or otherwise cause an electrical potential in the EA water relative to Earth ground, for example. The following discussion of the electroporation electrodes is made with reference to electrolysis unit 318 having electrode 348 (shown in FIG. 4) with the understanding the electroporation electrodes are applicable to each embodiment of the present disclosure.

The EA water exiting electrolysis cell 346 (or other electrochemically-treated or untreated liquid) may come into contact with electrode 348, where electrode 348 is configured to impart, induce or otherwise cause an electrical potential in the EA water flowing through fluid line 338. As discussed above, if the resulting electric field applied across the cells of the microorganism is of a sufficient magnitude, the electric field can cause irreversible damage or destruction to the microorganisms through a mechanism such as electroporation and/or electrohydraulic shock.

In one embodiment, electrode 348 is formed by an electrically conductive spike or "barb", which may be inserted through the side wall of fluid line 338 so a portion of electrode 348 comes into physical contact with EA water flowing through fluid line 338. In an alternative embodiment, fluid line 338 may be at least partially fabricated from of an electrically conductive material, such as a metal and/or a conductive polymer. For example, fluid line may 338 include a section made of copper, which is electrically connected to electrical line 348a In an exemplary embodiment, electrode 348 is separate from and external to electrolysis cell 346 and has no corresponding return electrode (e.g., an electrode of opposite polarity and/or an electrode representing a circuit ground for the electroporation electrode). Additional examples of suitable electrode designs for the electroporation electrodes of the present disclosure include those disclosed in U.S. patent application Ser. Nos. 12/639,622 and 12/639,628.

The power supply via electrical line 341 and/or control electronics 344 can be configured to deliver an AC and/or DC voltage (such as a positive voltage) to electrode 348, and thus to the EA water in fluid line 348. This additional electrical potential applied to the EA water can increase the electroporation/electrohydraulic shock inflicted on the microorganisms, for example. Various voltages and voltage patterns can be used in alternative embodiments. Furthermore, Earth ground may serve to complete the electrical circuit formed by electrode 348, the EA water delivered by the dispenser (e.g., dispenser 34), and the articles and the rotary tub (e.g., rotary tub 22).

The electrical characteristics of the driving voltage pattern may be based on the design of the apparatus and the method of application of the liquid to the microorganism. In one example, the driving voltage applied to the electrode may have a frequency in the range of 25 kilohertz to 800 kilohertz (KHz) and a voltage of 50 volts to 1000 volts root-mean-square (rms). However, the applied current can be very low, such as but not limited to the order of 0.15 milliamps. The voltage pattern can be a DC pattern, and AC pattern or a combination of both. The voltage waveform can be any suitable type such as square, sinusoidal, triangular, sawtooth, and/or arbitrary (from arbitrary pattern generator). In one example, the waveform sequentially changes between various waveforms. The positive (or alternatively negative) side of the voltage potential is applied to electrode 348, and the potential of the surface (or volume of space) being treated serves as the circuit ground (such as Earth ground), for example. In addition, the waveforms and voltage levels may affect different microorganisms differently. So these parameters can be modified to enhance killing of particular microorganisms or can be varied during application to treat effectively a variety of different organisms.

Examples of suitable voltages that may be applied to electrode 348 include but are not limited to AC voltages in a range of 50 volts rms to 1000 volts rms, 500 volts rms to 700 volts rms, or 550 volts rms to 650 volts rms. One particular embodiment applies an voltage of about 600 volts rms to electrode 348. Examples of frequencies for the voltage that may be applied to electrode 348 include but are not limited to those frequencies within a range of 20 KHz to 100 KHz, 25 KHz to 50 KHz, 30 KHz to 60 KHz, or about 28 Khz to about 40 KHz. One particular embodiment applies the voltage at about 30 KHz to electrode 348.

FIG. 6A is a waveform diagram illustrating the voltage pattern that may be applied electrode 348 in one particular example. In this example, the shape of the waveform is a combination of a sine wave and a square wave. However, the waveform can have other shapes, such as a sine wave, a square wave, or other waveform. The applied voltage has an AC voltage of 600 volts rms (about 1000V to 1200 volts peak-to-peak) when liquid is flowing through adapter 240 of the electrode and has a frequency of about 30 KHz. In this example, the frequency remains substantially constant as the apparatus (e.g., spray bottle) dispenses electrochemically-activated liquid to the surface being treated. In another example, the frequency is maintained in a range of about 41 KHz-46 KHz.

In another example, the frequency varies over a predefined range while the washing system (e.g., washing systems 10, 110, and 210) dispenses WA water to the surface being treated (e.g., articles in rotary tubs 22, 122, and 222). For example, the control electronics 344 can sweep the frequency within a range between a lower frequency limit and an upper frequency limit, such as between 20 KHz and 100 KHz, between 25 KHz and 50 KHz, and between 30 KHz and 60 KHz.

Figure 6A:
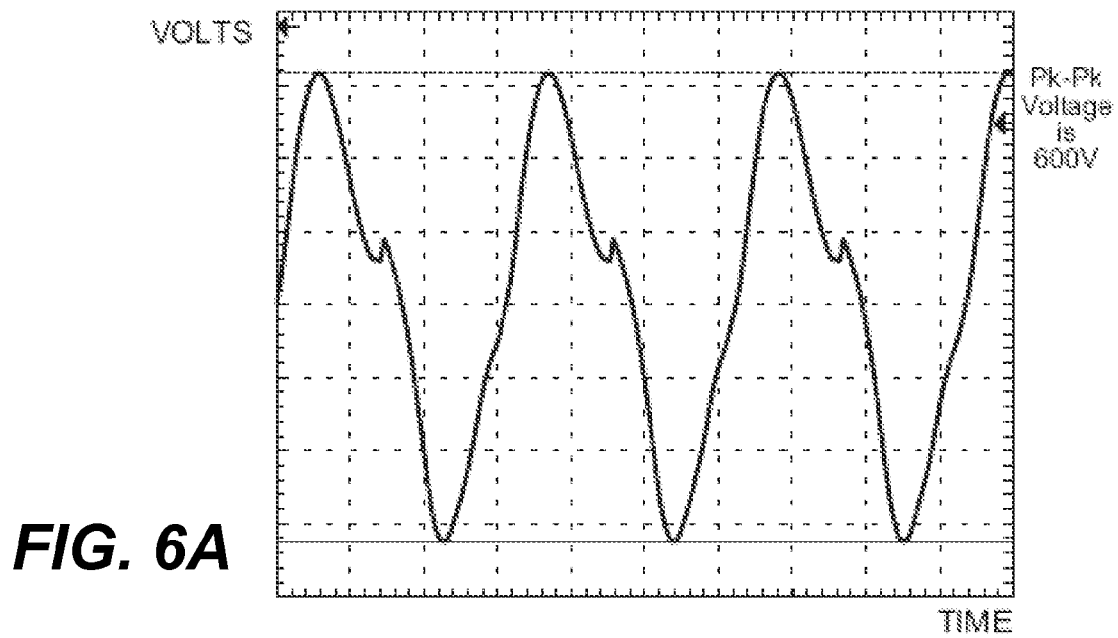
FIGS. 6A-6C are examples of waveform diagrams illustrating voltage patterns applied to electroporation electrodes in washing systems according to exemplary aspects of the present disclosure.
Figure 6B:
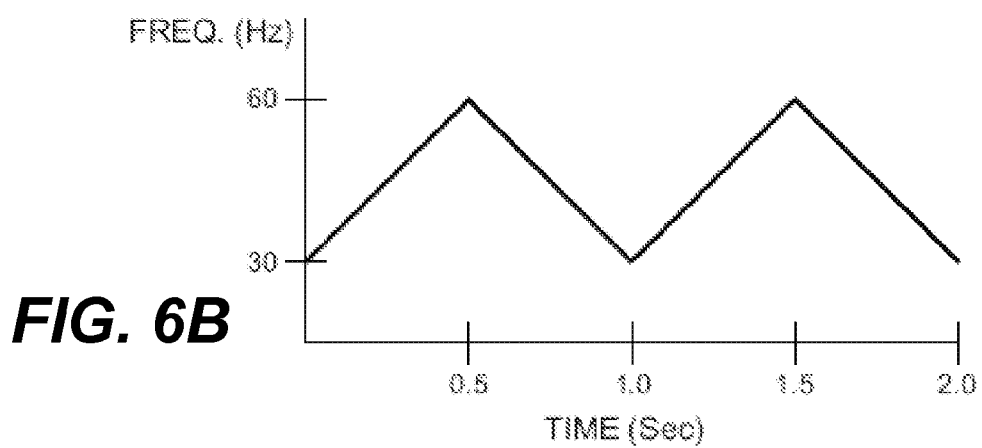

FIG. 6B is a waveform diagram illustrating the frequency with respect to time of the voltage applied to electrode 348 in another particular example. In this example, the frequency ramps, with a triangular waveform, from the low frequency limit to the high frequency limit and then back down to the low frequency limit over a period of about 1 second, for example. In another example, the control circuit ramps the frequency from the from the low frequency limit to the high frequency limit (and/or from the high frequency limit to the low frequency limit) over a time period of 0.1 second to 10 seconds. Other ramp frequency ranges can also be used, and the respective ramp-up and ramp-down periods can be the same or different from one another. Since different microorganisms might be susceptible to irreversible electroporation at different frequencies, the killing effect of the applied voltage is swept between different frequencies to potentially increase effectiveness on different microorganisms. For example, sweeping the frequency might be effective in applying the potential at different resonant frequencies of different microorganisms.

Figure 6C:
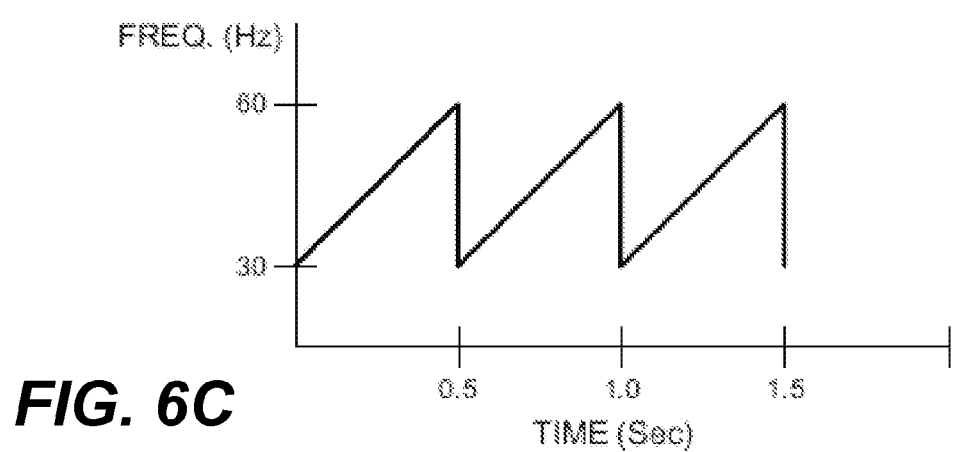

In the example shown in FIG. 6C, the frequency is swept between 30 KHz and 60 KHz with a sawtooth waveform. Other waveforms can also be used.

Figure 7A:
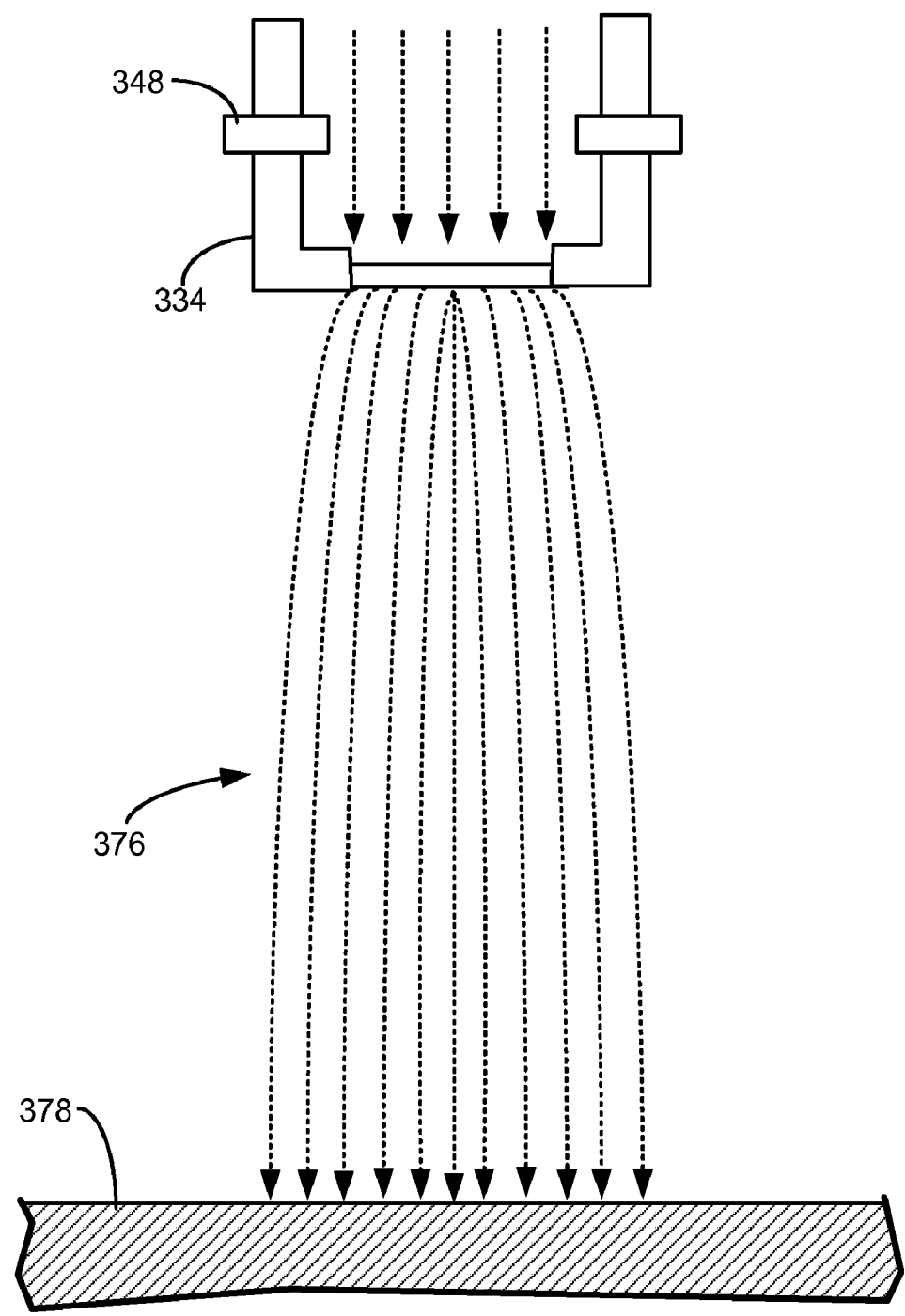
FIG. 7A is a diagram illustrating an example of conductive paths formed between a dispenser and a surface by an electrically charged output.

FIG. 7A is a diagram illustrating the output 376 being dispensed from dispenser 334, where individual droplets of output 376 may take different paths from dispenser 334 to surface 378 being treated. Dispenser 334 is a washing system dispenser (e.g., dispensers 34, 134, and 234), and contains electrode 348. Surface 378 may be a surface of a rotary tub of the washing system (e.g., rotary tubs 22, 122, and 222) and/or one or more articles retained in the rotary tub, and may or may not have an electrical conduction path to a ground, such as Earth ground. When dispensed from a dispenser into a rotary tub (e.g., from dispenser 34 into rotary tub 22, shown in FIG. 1), the charged EA water forms a conducting suspension medium, thereby forming an electrically conductive path from electrode 348 to the surface of the rotary tub and/or any articles retained in the rotary tub.

Figure 7B:
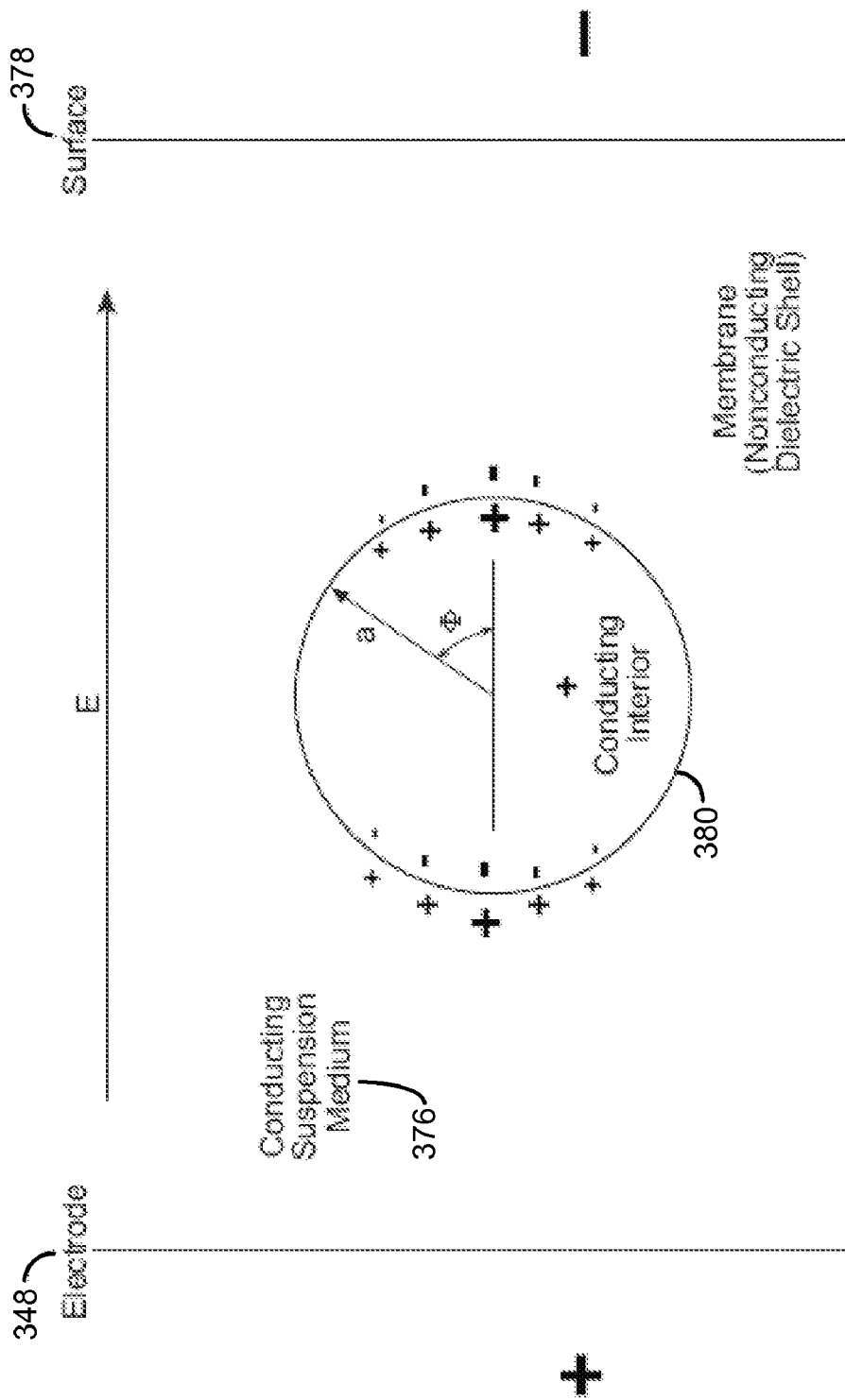
FIG. 7B is a diagram illustrating an example of an electroporation mechanism, whereby a cell suspended in a medium is subjected to an electric field.

FIG. 7B is a diagram illustrating an example of the electroporation mechanism achieved by dispensing output 376 to surface 378 (shown in FIG. 7A). As discussed above, output 376 dispensed on surface 378 has been found to form a conducting suspension medium. FIG. 7B illustrates the resulting electric field "E" applied to a cell membrane 380 of a microorganism that is suspended from surface 378 by the liquid from output 376. Output 376 and the liquid dispensed on surface 378 together form a conductive path from electrode 348 to surface 378, for example.

It is believed that the addition of an applied alternating potential from electrode 348 to the EA water endows the dispensed output with significantly enhanced sanitizing action. This phenomenon may be associated with irreversible electroporation. In one particular embodiment, the alternating potential appears to be particularly effective at 600 volts, 28 kHz with a variable effect for different organisms. However, other voltage and frequencies can be used in other embodiments.

Electroporation followed by cell death is achievable with a transmembrane potential of at least 0.5 volts (where a membrane thickness is typically about three nanometers, for example). Depending on the configuration, such potentials may require a pulse of about 10 kilovolts/centimeter or more. Lower potentials may be effective, for example in the presence of cell toxins or with the availability of additional mechanisms for preventing normally reversibly-formed pores from resealing. It should be noted that although electroporation is commonly used as a 'reversible' tool at lower potentials, it is recognized that, even under these conditions, often only a small percentage of cells recover.

Figure 7C:
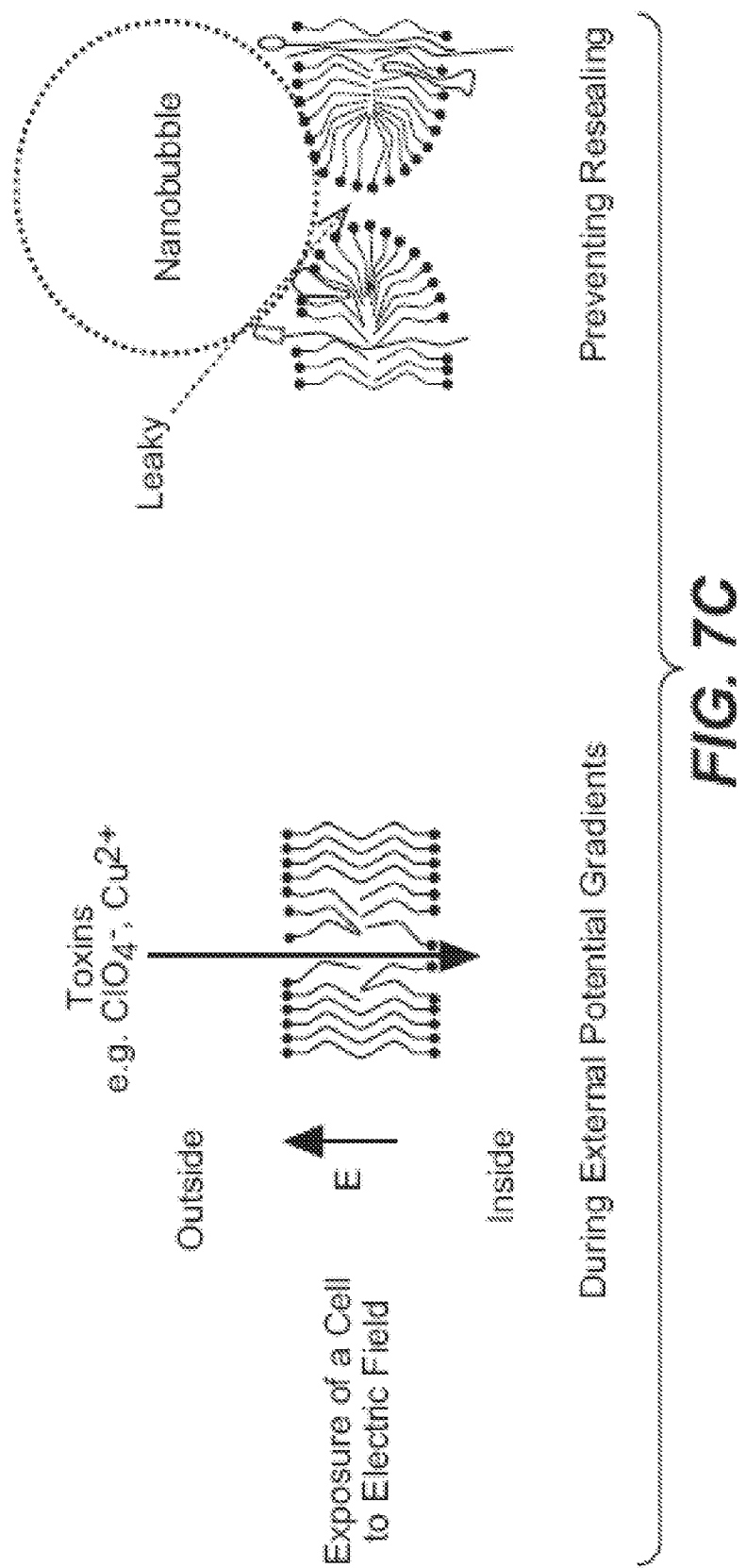
FIG. 7C is a diagram illustrating an example of a cell membrane having pores expanded by electroporation.

The formation of holes in the cell membranes is generally insufficient in itself to cause cell death, as cells can survive for relatively long periods with large amounts of membrane missing. Cell death comes because of disruption to the metabolic state of the cells, which can be caused by electrophoretic and electroosmotic (capillary electrophoretic) movement of materials into and out of the cells. Diffusion by itself is generally too slow. To achieve electrophoresis and electroosmosis, sufficient power should be dissipated within the surface, as shown in FIG. 7C.

Different microorganisms have different total surface charges and charge distributions and therefore will react differently to each other in terms of cell death. They will also behave differently in the oscillating potential field and will have different resonant frequencies for maximum absorption (and hence maximum movement relative to the aqueous solution, causing the maximum chaos to their metabolism). Movement in and out depends primarily on potential gradients. Increased effects occur when the system is in resonance.

The dispensed water droplets may descend at different rates, and the time differences may be significant when related to the rapidly alternating potential (e.g., 28 kHz). The descent velocity (dependent on the drop size, flow rate and nozzle diameter) will determine the difference in time between the drops landing but this is likely to be several to many times the potential cycling time of 36 microseconds.

Cells with open pores are much more prone to the effects of cell toxins in the charged EA water as they have no barrier to their entry. The potential cell toxins co-delivered with the alternating potential are peroxide, chlorine oxides, and other redox agents such as superoxide, ozone and singlet oxygen, and heavy metal ions such as cupric ions and/or silver ions. Charged nanobubbles will move in the electric fields and will be capable of picking up materials from the surface. As they are surface-active, they may additionally interfere with pore resealing and preferentially deliver their cytotoxic surface active molecules to the pore sites, as shown in FIG. 7C, for example.

In view of the above, the charged EA water acts as a cleaning agent due to production of tiny electrically-charged bubbles. These attach themselves to dirt particles/microorganisms so transferring their charge. The charged and coated particles separate one from another due to the repulsion between their similar charges and enter the solution as a suspension. Coating of the dirt by tiny bubbles promotes their pick-up by larger buoyant bubbles that are introduced during cleaning, thus aiding the cleaning process. Simultaneously, microorganisms can be electroporated and killed or otherwise eliminated by the electric potential generated by the additional electrode 334, thereby reducing the number of microorganisms on a surface. Thus, to enhance sanitization ability properties, electroporation can be used for example to accomplish a more consistent and effective destruction of microbial action by discharging (in a relative sense) a high-voltage to a ground (such as Earth ground) through e.g. an aqueous fluid.

It has also been found that the combination of the EA water produced by electrolysis cell 346 and the electric field applied by electrode 348 has a synergistic effect. It is believed that as the charged nanobubbles produced in the EA water move in the electric fields, they pick up microorganisms and separate them from the receiving surface and/or articles. By separating the microorganisms from the receiving surface and/or articles, such that they are suspended in the water, the electric field produced along the receiving surface and/or articles by electrode 348 is applied more easily across the microorganism cells. Whereas, if the microorganism is in contact with the receiving surface and/or articles, the electric field is more easily discharged into the surface ground and may be less effective in creating irreversible electroporation of the organisms cells. With the cell suspended, the applied alternating field oscillates back and forth causing damage to the cells.

Sink and Faucet-Type Washing Systems

Another aspect of the present disclosure relates to sink and faucet-type washing systems and methods of use with charged EA water, where the charged EA water may include a blend of an alkaline liquid and an acidic liquid. The following discussion of the charged EA liquid with the sink and faucet-type washing systems is also made with reference to water (e.g., charged EA water) with the understanding that the charged EA liquid of the present disclosure may obtained from a variety of different liquids. The use of the charged EA liquid/water may also be applied to shower and bath washing systems in similar manners to those discussed below for the sink and faucet-type washing systems.

FIGS. 8-12 illustrate the use of electrolysis cell assemblies with sink and faucet-type washing systems. As shown in FIG. 8, washing system 510 includes sink basins 512, liquid sources 514 and 516, electrolysis unit 518, and faucet assembly 520. Electrolysis unit 518 is an electrically-powered unit that may be secured to any suitable location between liquid source 514 and faucet assembly 520, and may operate in the same manner as discussed above for electrolysis unit 18 (shown in FIG. 1), electrolysis unit 318 (shown in FIG. 4), and electrolysis unit 418 (shown in FIG. 5). Electrolysis unit 518 may also be a self-contained unit connectable to a conventional water inlet line of faucet 530, and may be electrically connected to an external power supply (not shown) via electrical line 521.

As shown, faucet assembly 520 includes fluid lines 522, 524, 526, and 528, faucet 530, and sprayer 532, which may be arranged in a conventional manner. For example, fluid line 522 may be a hot water line that receives hot water from liquid source 514 via electrolysis cell 518, and supplies the hot water to faucet 530. Accordingly, fluid line 524 may be a hot water line that connects between fluid line 522 and a separate dish washing machine. In one embodiment, the dish washing machine may operate as discussed above, where the EA water may be received from electrolysis cell 518. Fluid line 524 may be a cold water line that receives cold water from liquid source 516, and supplies the cold water to faucet 530.

Faucet 530 includes actuator handle 534 and dispenser 536, and may operate in a conventional manner. Accordingly, upon actuation of actuator handle 534, water may flow from liquid source 514 into electrolysis cell 518. As discussed above, electrolysis cell 518 electrochemically activates the water, thereby providing EA water to faucet 530 via fluid line 522. Additionally, electrolysis unit 518 includes one or more electroporation electrodes (not shown) that may function in the same manner as electrode 48 (shown in FIG. 1), electrode 348 (shown in FIG. 4), and electrode 448 (shown in FIG. 4) to impart, induce or otherwise cause an electrical potential in the EA water relative to Earth ground.

The electroporation electrode of electrolysis unit 518 may be positioned at any suitable location downstream of the electrolysis cell of electrolysis unit 518, and is configured to make electrical contact with the EA water. For example, the electroporation electrode may be positioned at fluid line 522, fluid line 528, sprayer 532, and/or dispenser 536. In one embodiment, the electroporation electrode may be secured to sprayer 532 and/or dispenser 536 and an electrical line corresponding to electrical line **48*a* (shown in FIG. 1) may extend through sink basin 512 to the control electronics in electrolysis unit 518. Furthermore, the fluid path(s) downstream from the electroporation electrode are desirably electrically isolated to reduce the extent that the charged EA water is grounded prior to being dispensed from sprayer 532 and/or dispenser 536. For example, fluid line 528 and/or sprayer 532** may be fabricated from dielectric materials, which can electrically isolate the charged EA water.

A user may also redirect the flow of the EA water to sprayer 532, which may receive the EA water from faucet 530 via fluid line 528. Accordingly, as discussed below, in one suitable embodiment, the electroporation electrode is secured to sprayer 532, such as at a tip of sprayer 532. This embodiment allows sprayer 532 to function as a hand-held sprayer, as discussed in U.S. patent application Ser. Nos. 12/639,622 and 12/639,628.

Despite being blended together, the acidic water and alkaline water retain their ionic properties and gas-phase bubbles for a sufficient duration to be dispensed from dispenser 536 and/or sprayer 532. The charged EA water may then be used to clean a variety of items without requiring the use of chemical cleaning products (e.g., soaps and detergents). This is particularly suitable for cleaning food-based items, such as fruits and vegetables, which may otherwise absorb and retain chemical cleaning products.

FIG. 9 illustrates washing system 610, which is a second washing system to washing system 510 (shown in FIG. 8), where corresponding reference labels are increased by "100". As shown in FIG. 9, washing system 610 further includes electrolysis unit 638, where electrolysis unit 638 may be secured to any suitable location between liquid source 616 and faucet assembly 620, and may operate in the same manner as discussed above for electrolysis unit 18 (shown in FIG. 1), electrolysis unit 318 (shown in FIG. 4), and an electrolysis unit containing electrolysis cell 446 (shown in FIG. 5).

Electrolysis unit 638 may also be a self-contained unit connectable to a conventional water inlet line of faucet 630, and may be electrically connected to an external power supply (not shown) via electrical line 639. Accordingly, the embodiment shown in FIG. 7 allows a pair of electrolysis cells to be incorporated in the same manner as discussed above for washing system 210 (shown in FIG. 2). This arrangement allows the water streams from liquid sources 614 and 616 to selectively undergo electrolysis processes, independent of each other, to generate EA water streams. Furthermore, the electroporation electrode(s) (not shown) of electrolysis units 518 and 638 may be positioned at any suitable locations downstream of the electrolysis cells of electrolysis unit 518 and 638, and are configured to make electrical contact with the EA water to impart, induce or otherwise cause an electrical potential in the EA water.

FIG. 10 illustrates washing system 710, which is a third washing system to washing system 510 (shown in FIG. 8), where corresponding reference labels are increased by "200". As shown in FIG. 10, washing system 710 includes electrolysis unit 740 in lieu of (and/or in addition to) electrolysis units 518, 618, and 638. In this embodiment, electrolysis unit 740 may be secured to any suitable location between faucet 730 and sprayer 732, thereby allowing the water stream that is redirected to sprayer 730 to undergo an electrolysis process. This allows the hot and/or cold water redirected to sprayer 730 to undergo an electrolysis process with a single electrolysis unit, separate from the water being dispensed from dispenser 736.

In one embodiment, electrolysis unit 740 may also be in electrical communication with sprayer 732, thereby allowing activation of electrolysis unit 740 to coincide with the operation of sprayer 732. This communication is beneficial for regulating the operation of electrolysis unit 740 when sprayer 732 redirects the water to flow through fluid line 728. Additionally, the electroporation electrode (not shown) of electrolysis unit 740 may be positioned at any suitable location downstream of the electrolysis cell of electrolysis unit 740, such as along fluid line 728 and/or at sprayer 732. This allows the electroporation electrode to make electrical contact with the EA water flowing through fluid line 728 and/or sprayer 732 to impart, induce or otherwise cause an electrical potential in the EA water prior to being sprayed.

Figure 8:
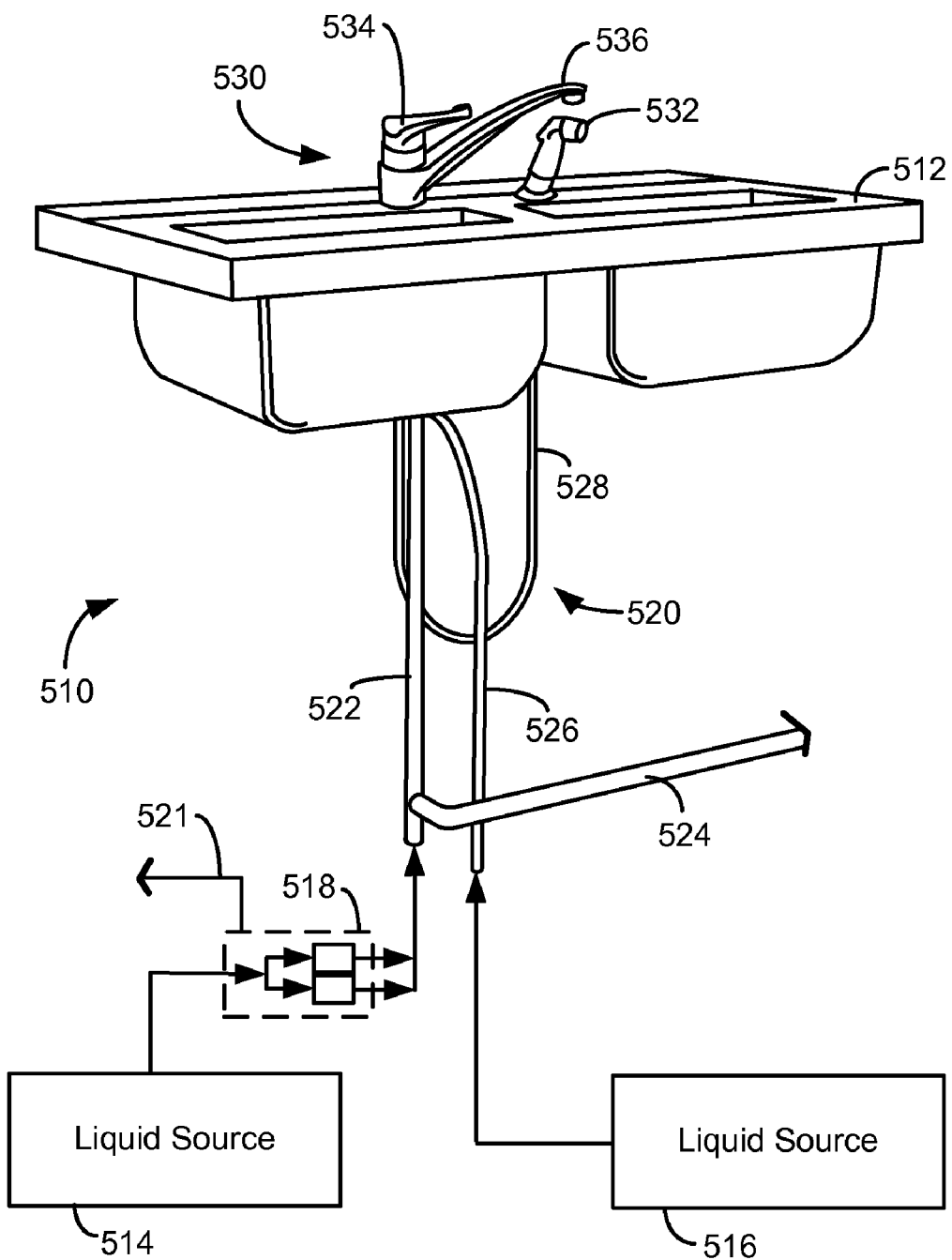
FIG. 8 is a perspective view of a first faucet assembly in use with a sink arrangement, where the faucet assembly includes an external electrolysis unit.
Figure 9:
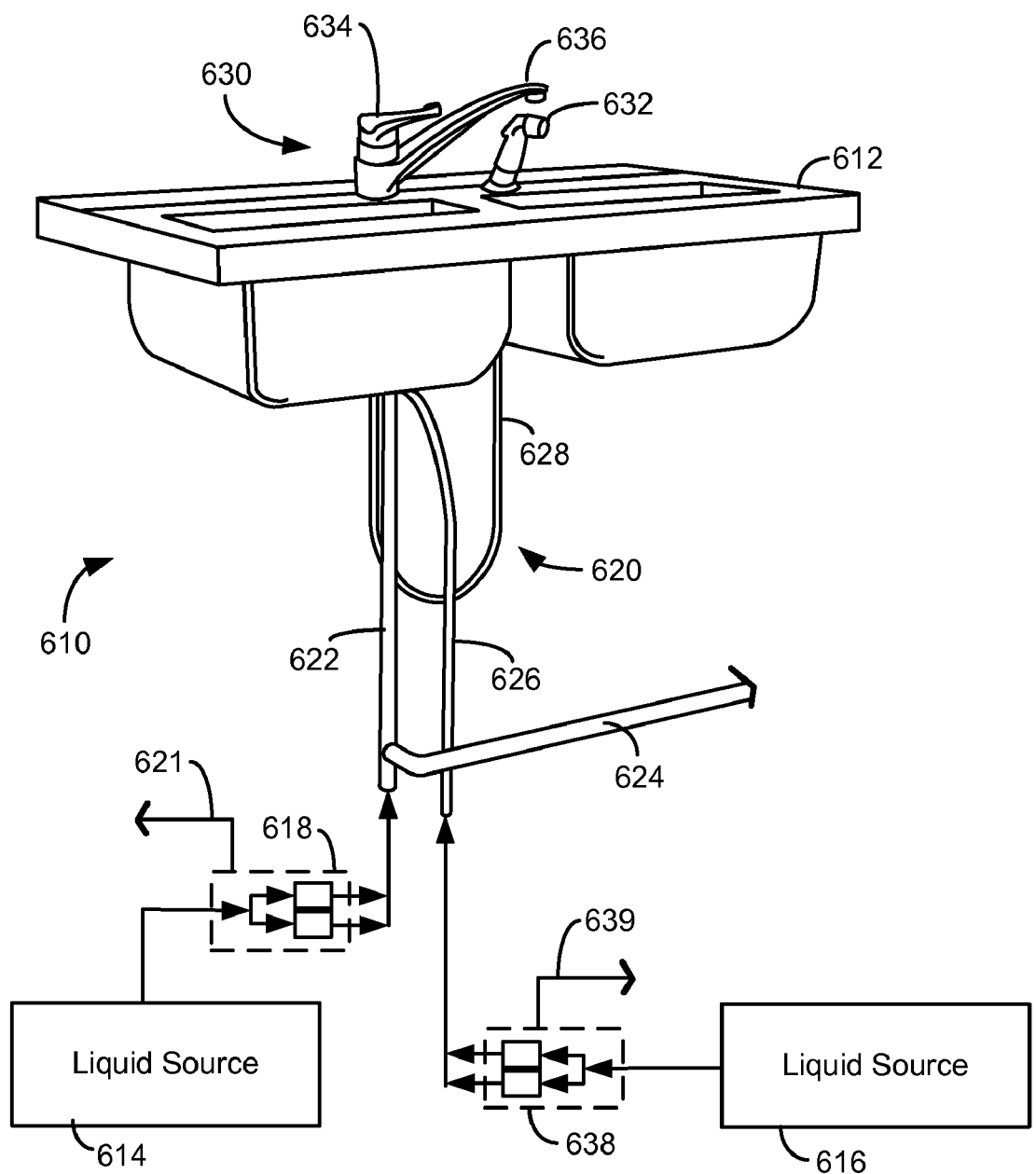
FIG. 9 is a perspective view of a second faucet assembly in use with a sink arrangement, where the faucet assembly includes a pair of external electrolysis units.
Figure 11:
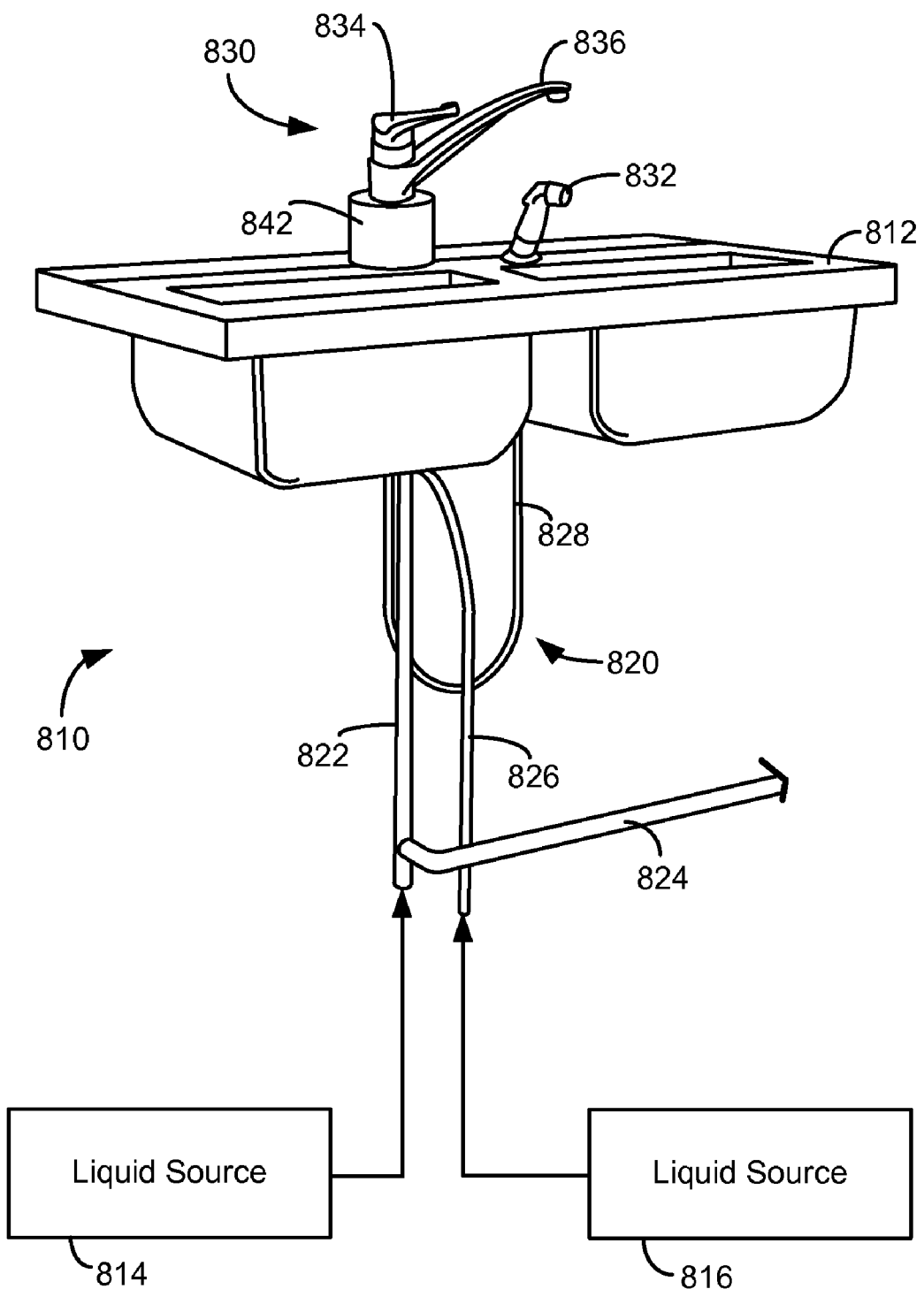
FIG. 11 is a perspective view of a fourth faucet assembly in use with a sink arrangement, where the faucet assembly includes an integral electrolysis unit.

FIG. 11 illustrates washing system 810, which is a fourth washing system to washing system 510 (shown in FIG. 8), where corresponding reference labels are increased by "300". As shown in FIG. 11, washing system 810 includes electrolysis unit 842 in lieu of (and/or in addition to) electrolysis units 518, 618, 638, and 740. In this embodiment, electrolysis unit 842 may be integrally connected to faucet 830, which also allows the hot and/or cold water to undergo an electrolysis process with a single electrolysis unit.

Furthermore, electrolysis unit 842 may also be in electrical communication with actuator handle 834, thereby allowing activation of electrolysis unit 842 to coincide with the operation of actuator handle 834. For example, handle actuator 834 may actuate a switch that energizes electrolysis unit 842 when water flows through dispenser 836 and/or sprayer 832, and de-energizes electrolysis unit 842 when water does not flow through dispenser 836 and/or sprayer 832. This communication is beneficial for regulating the operation of electrolysis unit 842 when faucet 830 is being used.

Additionally, the electroporation electrode (not shown) of electrolysis unit 842 may be positioned at any suitable location downstream of the electrolysis cell of electrolysis unit 842, such as at dispenser 836. This allows the electroporation electrode to make electrical contact with the EA water flowing through dispenser 836 to impart, induce or otherwise cause an electrical potential in the EA water prior to being dispensed.

Figure 12:
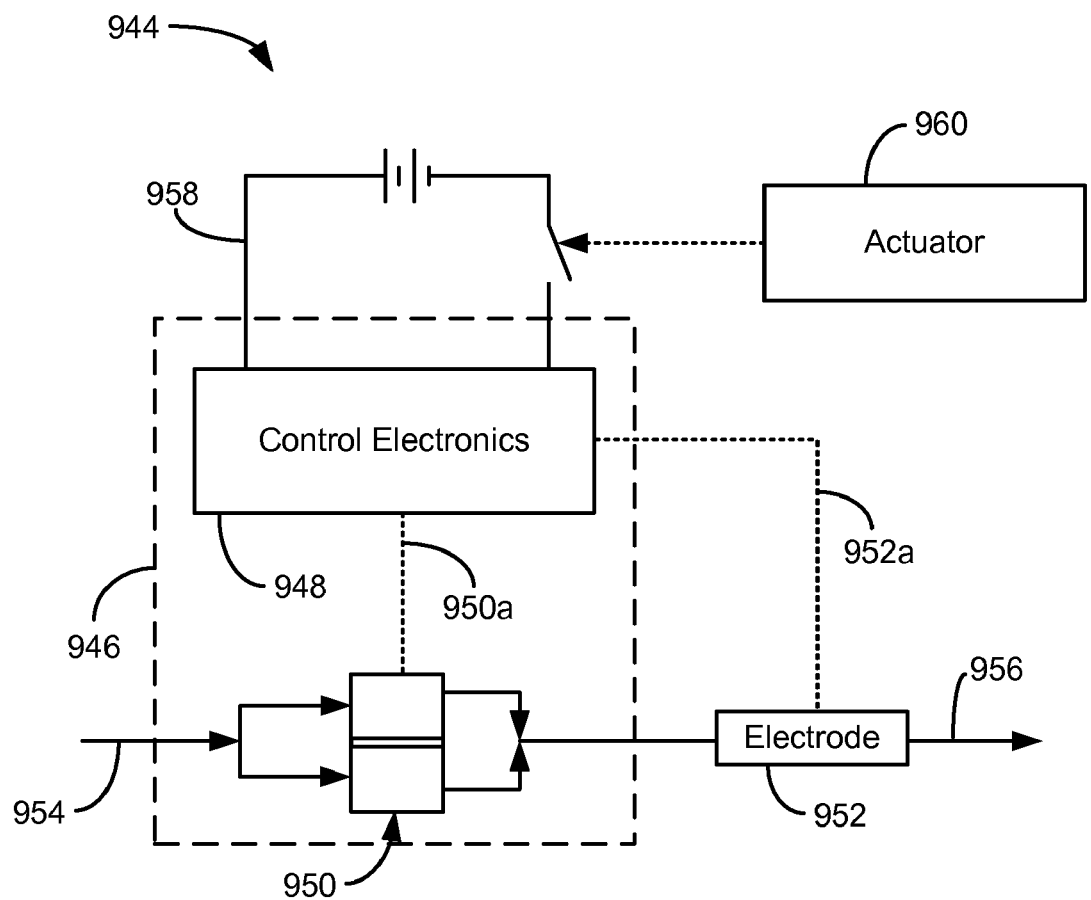
FIG. 12 is a schematic diagram illustrating an electrolysis unit of a faucet assembly in use with an actuator of the faucet assembly.

FIG. 12 is a schematic diagram illustrating electrolysis unit 944, which is a suitable design for electrolysis units 518, 618, 638, 740, and 842. As shown in FIG. 12, electrolysis unit 944 includes housing 946, control electronics 948, electrolysis cell 950, and electrode 952, and may function in the same manner as electrolysis unit 18 (shown in FIG. 1), electrolysis unit 318 (shown in FIG. 4), and electrolysis unit 418 (shown in FIG. 5).

Figure 10:
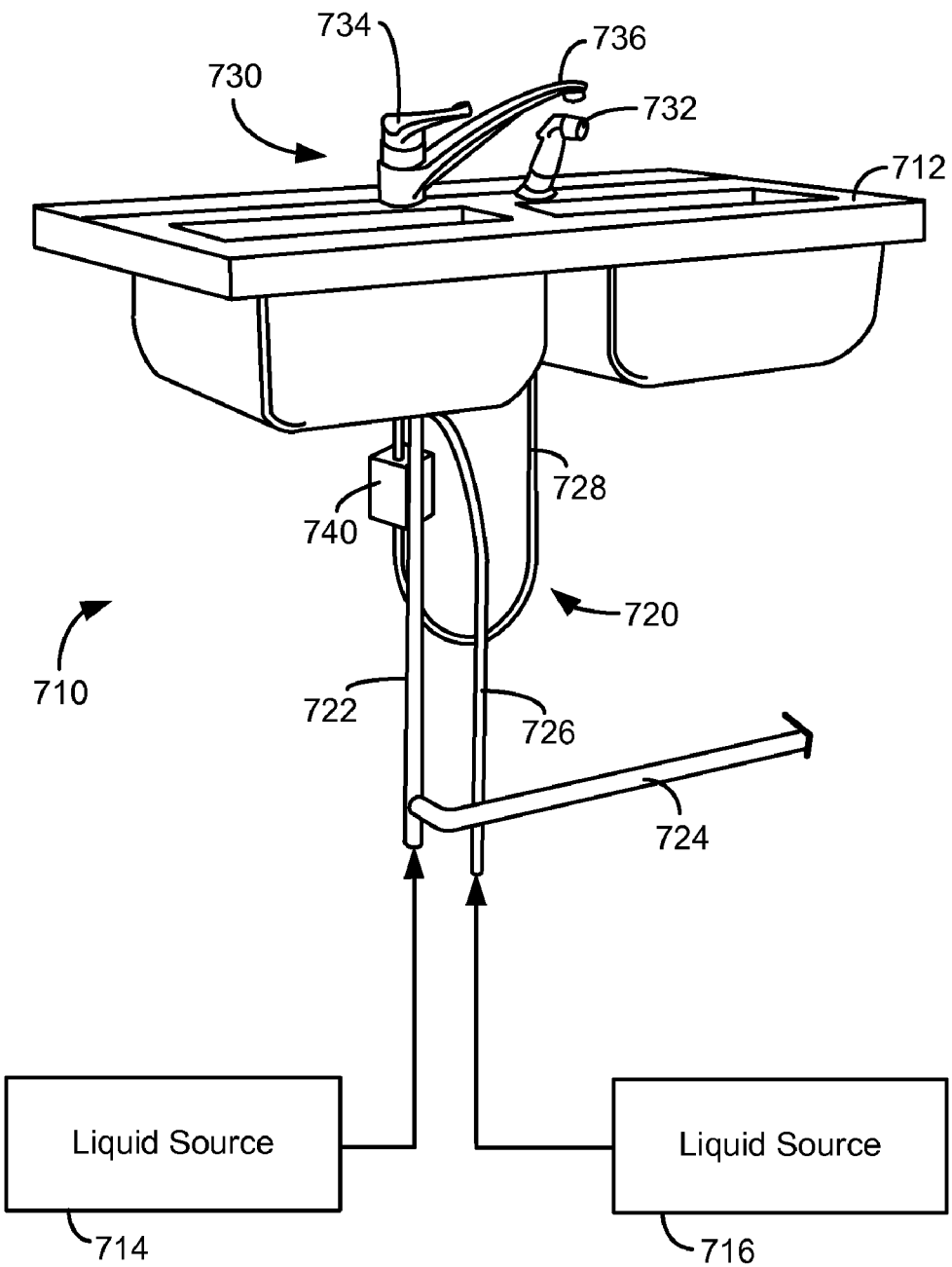
FIG. 10 is a perspective view of a third faucet assembly in use with a sink arrangement, where the faucet assembly includes an external electrolysis unit secured to a sprayer fluid line.

Housing 946 may be secured between fluid lines 954 and 956, where fluid lines 954 and 956 may be one or more fluid lines of systems 510, 610, 710 and 810, depending on the location of electrolysis unit 944. For example, in the embodiment shown in FIG. 8 where electrolysis unit 944 corresponds to electrolysis unit 518, fluid line 954 may interconnect liquid source 514 with electrolysis unit 518/944, and fluid line 956 may correspond to fluid line 522. Alternatively, in the embodiment shown in FIG. 10, where electrolysis unit 944 corresponds to electrolysis unit 740, fluid line 954 may correspond to an upstream portion of fluid line 728 relative to electrolysis unit 740/944, and fluid line 956 may correspond to a downstream portion of fluid line 728 relative to electrolysis unit 740/944 and connecting to sprayer 732.

Control electronics 948 may direct the operation of electrolysis unit 944 in the same manner as discussed above for control electronics 48 (shown in FIG. 1), electronics 348 (shown in FIG. 4), and electronics 448 (shown in FIG. 5), and is configured to relay electrical power from electrical line 958 to electrolysis cell 950 (via electrical line 950$a$) and to electrode 952 (via electrical line 952$a$) during operation.

Electrode 952 is an electrical conductor, lead, or other electrical and/or electromagnetic component, which is positioned along fluid line 956 to impart, induce or otherwise cause an electrical potential in the EA water flowing through fluid line 956 relative to Earth ground. Accordingly, as discussed above, electrode 952 may be positioned at any suitable location downstream of electrolysis cell 950. For example, electrode 952 may be positioned at a fluid line (e.g., fluid lines 522, 528, 622, 626, 628, and 728), at a sprayer (e.g., sprayers 532, 632, 732, and 832), and/or at a dispenser (e.g., dispensers 536, 636, 736, and 836).

As further shown in FIG. 12, actuator 960 is coupled in series between the power supply from electrical line 958 and control electronics 948, and serves to couple and decouple the power supply to and from power inputs of control electronics 948 depending on the state of actuator 960. In this embodiment, actuator 960 may correspond to an actuator handle (e.g., actuator handles 534, 634, 734, and 834), a sprayer trigger (e.g., triggers of sprayers 532, 632, 732, and 832), and/or other similar actuating device.

For example, in an embodiment in which actuator corresponds to a spray trigger of sprayer 532 (shown in FIG. 8), when turns faucet assembly 530 on to have water flow through at least fluid line 522 from liquid source 514, the user may also depress the spray trigger (i.e., actuator 960) of sprayer 532. This closes the circuit of electrical line 958, thereby allowing control electronics 948 to energize electrolysis cell 950 and electrode 952. The resulting water flowing through electrolysis cell and past electrode 952 is then respectively electrochemically activated and charged to provide charged EA water to be sprayed from sprayer 532. When pressure is removed from the spray trigger (i.e., from actuator 960), the circuit of electrical line 958 is opened, thereby causing control electronics 948 to de-energize electrolysis cell 950 and electrode 952. Thus, the water that continues to flow through dispenser 536 is not charged or electrochemically activated. This arrangement allows a user to control when the charged EA water is to be dispensed for cleaning articles in sink basins 512.

Although the present disclosure has been described with respect to several embodiments, workers skilled in the art will recognize that changes may be made in form and detail without departing from the spirit and scope of the disclosure.

The invention claimed is:

1. A washing system comprising:
   a washing machine vessel;
   a fluid-treatment component operably coupled to a fluid line and located upstream from the washing machine vessel, the fluid-treatment component being configured to activate a liquid received from the fluid line to produce an activated liquid;
   a dispenser located downstream from the fluid-treatment component, the dispenser being configured to dispense the activated liquid into the washing machine vessel;
   an electrode located downstream from the fluid-treatment component and upstream from or integra; with the dispenser, the electrode being configured to be in electrical contact the with the activated liquid;
   at least one control circuit configured to apply a voltage to the electrode to generate an alternating electrical field through the dispensed activated liquid between the electrode and the washing machine vessel; and a regulator unit configured to regulate liquid flows between the fluid line and the dispenser, wherein the at least one control circuit is further configured to operate the regulator unit to direct liquid flows to the dispenser while applying the voltage to the electrode.

2. The washing system of claim 1, wherein the fluid-treatment component comprises an electrolysis cell, and wherein the at least one control circuit is further configured to generate an electrical field in the electrolysis cell.

3. The washing system of claim 2, wherein the electrolysis cell comprises:
a chamber;
an anode electrode disposed within the chamber, and configured to be electrically connected to the at least one control circuit; and
a cathode electrode disposed within the chamber, and configured to be electrically connected to the at least one control circuit.

4. The washing system of claim 1, wherein the component comprises a media container configured to retain media that is configured to activate the received liquid.

5. The washing system of claim 4, wherein the media comprises at least one material selected from the group consisting of zeolites, ion-exchange resins, and combinations thereof.

6. The washing system of claim 1, wherein the washing system comprises a single-cycle washing system.

7. The washing system of claim 1, wherein the electrode is an integral component of the dispenser.

8. The washing system of claim 1, wherein the alternating electrical field has a frequency ranging from about 20 kilohertz to about 100 kilohertz.

9. A washing system comprising:
a washing machine vessel;
a fluid-treatment component operably coupled to a fluid line and located upstream from the washing machine vessel, the fluid-treatment component being configured to activate a liquid received from the fluid line to produce an activated liquid;
a dispenser located downstream from the fluid-treatment component and upstream from the washing machine vessel, the dispenser being configured to dispense the activated liquid into the washing machine vessel;
a regulator unit configured to regulate liquid flows between the fluid line and the dispenser;
an electrode located downstream from the fluid-treatment component and upstream from or integral with the dispenser, the electrode being configured to be in electrical contact the with the activated liquid; and
at least one control circuit configured to apply a voltage to the electrode to generate an alternating electrical field through the dispensed activated liquid between the electrode and the washing machine vessel, wherein the at least one control circuit is further configured to operate the regulator unit to direct liquid flows to the dispenser while applying the voltage to the electrode.

10. The washing system of claim 9, wherein the fluid-treatment component comprises an electrolysis cell, and wherein the at least one control circuit is further configured to generate an electrical field in the electrolysis cell when operating the regulator unit to direct liquid flows to the dispenser.

11. The washing system of claim 10, wherein the electrolysis cell comprises:
a chamber;
an anode electrode disposed within the chamber, and configured to be electrically connected to the at least one control circuit; and
a cathode electrode disposed within the chamber, and configured to be electrically connected to the at least one control circuit.

12. The washing system of claim 9, wherein the alternating electrical field has a frequency ranging from about 20 kilohertz to about 100 kilohertz.

13. A washing system comprising:
a machine housing;
a washing machine vessel retained within the machine housing;
a fluid-treatment component operably coupled to a fluid line and located upstream from the washing machine vessel, the fluid-treatment component being configured to activate a liquid received from the fluid line to produce an activated liquid;
a dispenser located downstream from the fluid-treatment component and upstream from the washing machine vessel, the dispenser being configured to dispense the activated liquid into the washing machine vessel;
a regulator unit retained within the machine housing, the regulator unit being configured to regulate liquid flows between the fluid line and the dispenser;
an electrode located downstream from the fluid-treatment component and upstream from or integral with the dispenser, the electrode being configured to be in electrical contact the with the activated liquid; and
at least one control circuit retained within the machine housing and outside of the washing machine vessel, the at least one control circuit being configured to apply a voltage to the electrode to generate an alternating electrical field through the dispensed activated liquid between the electrode and the washing machine vessel, wherein the at least one control circuit is further configured to operate the regulator unit to direct liquid flows to the dispenser while applying the voltage to the electrode.

14. The washing system of claim 13, wherein the fluid-treatment component comprises an electrolysis cell, and wherein the at least one control circuit is further configured to generate an electrical field in the electrolysis cell when operating the regulator unit to direct liquid flows to the dispenser.

15. The washing system of claim 14, wherein the electrolysis cell comprises:
a chamber;
an anode electrode disposed within the chamber, and configured to be electrically connected to the at least one control circuit; and
a cathode electrode disposed within the chamber, and configured to be electrically connected to the at least one control circuit.

16. The washing system of claim 13, wherein the component comprises a media container configured to retain media that is configured to activate the received liquid.

17. The washing system of claim 16, wherein the media comprises at least one material selected from the group consisting of zeolites, ion-exchange resins, and combinations thereof.

18. The washing system of claim 13, wherein the fluid-treatment component is retained within the machine housing and outside of the washing machine vessel.

19. The washing system of claim 13, wherein the alternating electrical field has a frequency ranging from about 20 kilohertz to about 100 kilohertz.

* * * * *